United States Patent
Blondel et al.

(10) Patent No.: US 11,406,631 B2
(45) Date of Patent: Aug. 9, 2022

(54) HYDRAZONE DERIVATIVES FOR PREVENTING OR TREATING EBV-RELATED CANCERS

(71) Applicants: Universite de Bretagne Occidentale, Brest (FR); Centre Hospitalier Regional Universitaire de Brest, Brest (FR); Institut National de la Sante et de la Recherche Medicale (INSERM), Paris (FR); Centre National de la Recherche Scientifique (CNRS), Paris (FR); Institut Curie, Paris (FR); Université de Paris, Paris (FR); Univ Paris XIII Paris-Nord Villetaneuse, Villetaneuse (FR); Universite Paris-Saclay, Saint Aubin (FR)

(72) Inventors: Marc Blondel, Brest (FR); Alicia Quillevere, Guipavas (FR); Cécile Voisset, Brest (FR); Maria José Lista, Paris (FR); Robin Fahraeus, Paris (FR); Chrysoula Daskalogianni, Paris (FR); Rodrigo Prado-Martins, Paris (FR); Marie-Paule Teulade-Fichou, Paris (FR); Anton Granzhan, Courbevoie (FR); Claire Beauvineau, Chilly Mazarin (FR); Oksana Reznichenko, Saint-Rémy-les-Chevreuse (FR)

(73) Assignees: Universite de Bretagne Occidentale; Centre Hospitalier Regional Universitaire de Brest; Institut National de la Sante et de la Recherche Medicale (INSERM); Centre National de la Recherche Scientifique (CNRS) (FR); Institut Curie; Université de Paris; Univ Paris XIII Paris-Nord Villetaneuse; Universite Paris-Saclay

( * ) Notice: Subject to any disclaimer, the term of this patent is extended or adjusted under 35 U.S.C. 154(b) by 15 days.

(21) Appl. No.: 17/045,049

(22) PCT Filed: Apr. 3, 2019

(86) PCT No.: PCT/EP2019/058435
§ 371 (c)(1),
(2) Date: Oct. 2, 2020

(87) PCT Pub. No.: WO2019/193071
PCT Pub. Date: Oct. 10, 2019

(65) Prior Publication Data
US 2021/0161887 A1 Jun. 3, 2021

(30) Foreign Application Priority Data
Apr. 3, 2018 (EP) .................. 18305392

(51) Int. Cl.
*A61K 31/4709* (2006.01)
*A61P 31/20* (2006.01)
(Continued)

(52) U.S. Cl.
CPC ........ *A61K 31/4709* (2013.01); *A61K 9/0019* (2013.01); *A61K 31/444* (2013.01);
(Continued)

(58) Field of Classification Search
None
See application file for complete search history.

(56) References Cited

FOREIGN PATENT DOCUMENTS

| CN | 105777783 B | 8/2017 |
|----|-------------|--------|
| WO | 2018211148 A1 | 11/2018 |

OTHER PUBLICATIONS

International Search Report for PCT/EP2019/058435 dated May 20, 2019; 5 pages.
(Continued)

*Primary Examiner* — Brian J Davis
(74) *Attorney, Agent, or Firm* — Lerner, David, Littenberg, Krumholz & Mentlik, LLP

(57) ABSTRACT

The present invention relates to novel bis-hydrazone derivatives of formula (I):

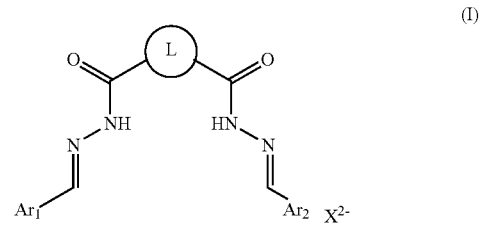

wherein $Ar_1$ and $Ar_2$ may be identical or different and are each independently selected from the group consisting of groups of formula (II) and (III):

(Continued)

-continued

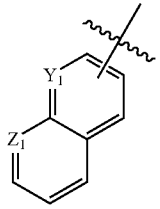

(III)

$Y_1$ and $Z_1$ are independently CH or $NR_c^+$, provided that al least one of $Y_1$ and $Z_1$ is $NR_c^+$ and at least one of $Y_1$ and $Z_1$ is CH,
and $R_a$, $R_b$, $R_c$, $X^{2-}$ and L as defined in the claims, or a hydrate or a solvate thereof.
Compositions and kits comprising same are also described. Said bis-hydrazone derivatives of formula (I), compositions and kits are useful as drugs, in particular for treating or preventing cancers associated with the Epstein-Barr Virus.

23 Claims, 6 Drawing Sheets

Specification includes a Sequence Listing.

(51) Int. Cl.
  A61P 35/00   (2006.01)
  A61K 9/00    (2006.01)
  A61K 31/444  (2006.01)
  A61K 31/4745 (2006.01)
  A61K 31/506  (2006.01)
  A61K 45/06   (2006.01)
  C07D 401/14  (2006.01)
  C07D 471/04  (2006.01)
(52) U.S. Cl.
  CPC ........ *A61K 31/4745* (2013.01); *A61K 31/506* (2013.01); *A61K 45/06* (2013.01); *A61P 31/20* (2018.01); *A61P 35/00* (2018.01); *C07D 401/14* (2013.01); *C07D 471/04* (2013.01)

(56) References Cited

OTHER PUBLICATIONS

European Search Report for EP18305392 completed Sep. 19, 2018; 3 pages.
Joan L. Buss et.al.: "The role of iron chelation in cancer therapy". Current Medicinal Chemistry, vol. 10(12). Jun. 1, 2003. pp. 1021-1034. XP002784895.
Gierczyk B, Zalas M. "Synthesis of substituted 1, 3, 4-thiadiazoles using Lawesson's reagent." Organic Preparations and Procedures International: The New Journal for Organic Synth. Organic Preparation and Procedures Co., Newton Highlands. MA. US Jun. 1, 2005;37(3):213-22. XP009144134.
Kaplanek Robert et al: "Synthesis and biological activity evaluation of hydrazone derivatives based on a Trager's base skele". Bioorganic & Medicinal Chemistry. Pergamon. GB. vol. 23. No. 7. Jan. 23, 2015 (Jan. 23, 2015). pp. 1651-1659. XP029204964.
Zhao Y et al: "A highly selective fluorescent chemosensor for Al+3 derivated from a-hydroxyquinoline". Inorganic Chemistry Communications. Elsevier. Amsterdam. NL. vol. 9. No. 9. Sep. 1, 2006 (Sep. 1, 2006). pp. 966-968. XP028039815.
Murat P, Balasubramanian S. Existence and consequences of G-quadruplex structures in DNA. Current opinion in genetics & development. Apr. 1, 2014;25:22-9.
Lista MJ, Voisset C, Contesse MA, Friocourt G, Daskalogianni C, Bihel F, Fåhraeus R, Blondel M. The long-lasting love affair between the budding yeast *Saccharomyces cerevisiae* and the Epstein-Barr virus. Biotechnology journal. Sep. 2015;10(11):1670-81.
Voisset C, Daskalogianni C, Contesse MA, Mazars A, Arbach H, Le Cann M, Soubigou F, Apcher S, Fahraeus R, Blondel M. A yeast-based assay identifies drugs that interfere with immune evasion of the Epstein-Barr virus. Disease models & mechanisms. Apr. 1, 2014;7(4):435-44.
Tosoni E, Frasson I, Scalabrin M, Perrone R, Butovskaya E, Nadai M, Palú G, Fabris D, Richter SN. Nucleolin stabilizes G-quadruplex structures folded by the LTR promoter and silences HIV-1 viral transcription. Nucleic acids research. Oct. 15, 2015;43(18):8884-97.
Lista MJ, Martins RP, Billant O, Contesse MA, Findakly S, Pochard P, Daskalogianni C, Beauvineau C, Guetta C, Jamin C, Teulade-Fichou MP. Nucleolin directly mediates Epstein-Barr virus immune evasion through binding to G-quadruplexes of EBNA1 mRNA. Nature communications. Jul. 7, 2017;8(1):1-3.
Akao I, Sato Y, Mukai K, Uhara H, Furuya S, Hoshikawa T, Shimosato Y, Takeyama I. Detection of Epstein-Barr virus DNA in formalin-fixed paraflin-embedded tissue of nasopharyngeal carcinoma using polymerase chain reaction and in situ hybridization. The Laryngoscope. Mar. 1, 1991;101(3):279-83.
Chang KL, Chen YY, Shibata D, Weiss LM. Description of an in situ hybridization methodology for detection of Epstein-Barr virus RNA in paraffin-embedded tissues, with a survey of normal and neoplastic tissues. Diagnostic molecular pathology: the American journal of surgical pathology, part B. Dec. 1, 1992;1(4):246-55.
Weiss LM, Movahed LA, Butler AE, Swanson SA, Frierson Jr HF, Cooper PH, Colby TV, Mills SE. Analysis of lymphoepithelioma and lymphoepithelioma-like carcinomas for Epstein-Barr viral genomes by in situ hybridization. The American journal of surgical pathology. Aug. 1, 1989;13(8):625-31.
Grasser, F. A., et al. "Monoclonal antibodies directed against the Epstein-Barr virus-encoded nuclear antigen 1 (EBNA1): immunohistologic detection of EBNA1 in the malignant cells of Hodgkin's disease." BLOOD, 84 (1994) 3792-3798.
Largy E, Hamon F, Teulade Fichou MP. Development of a high throughput G4-FID assay for screening and evaluation of small molecules binding quadruplex nucleic acid structures. Analytical and bioanalytical chemistry. Jul. 2011;400(10):3419-27.

Prior art

```
                         SEQUENCE LISTING

<160> NUMBER OF SEQ ID NOS: 3

<210> SEQ ID NO 1
<211> LENGTH: 18
<212> TYPE: RNA
<213> ORGANISM: Artificial
<220> FEATURE:
<223> OTHER INFORMATION: Primer

<400> SEQUENCE: 1
ggggcaggag caggagga                                               18

<210> SEQ ID NO 2
<211> LENGTH: 18
<212> TYPE: RNA
<213> ORGANISM: Artificial
<220> FEATURE:
<223> OTHER INFORMATION: Primer

<400> SEQUENCE: 2
ggggcaggag caggagga                                               18

<210> SEQ ID NO 3
<211> LENGTH: 26
```

```
<212> TYPE: DNA
<213> ORGANISM: Artificial
<220> FEATURE:
<223> OTHER INFORMATION: Primer

<400> SEQUENCE: 3
caatcggatc gaattcgatc cgattg                                        26
```

HYDRAZONE DERIVATIVES FOR PREVENTING OR TREATING EBV-RELATED CANCERS

FIELD OF INVENTION

The present invention relates to novel hydrazone derivatives, in particular cationic N-acylhydrazone derivatives, useful for treating or preventing cancers associated with the Epstein-Barr Virus (EBV-related cancers) by interfering with the interaction between the host cell protein nucleolin (NCL) and the virus-encoded EBNA1 mRNA in order to unveil tumour cells from EBV-related cancers to the immune system.

TECHNOLOGICAL BACKGROUND

The Epstein-Barr virus (EBV) is the first oncogenic virus discovered in human and has been linked to various cancers that include Burkitt and Hodgkin lymphomas and 10% of gastric cancers. Another example is the nasopharyngeal carcinoma which is particularly frequent among men in China and Tunisia. Like all the gammaherpesviruses, EBV evades the host immune system but has an Achilles heel: its genome maintenance protein (GMP) EBNA1. Indeed, EBNA1 is essential for EBV genome replication and maintenance and as such expressed in all dividing EBV-infected cells. On the other hand, EBNA1 is highly antigenic and CD8+ T cells directed towards EBNA1 epitopes exist in all infected individuals. Hence, EBV has evolved a mechanism to limit EBNA1 production to the minimal level required for the viral genome replication and, at the same time, to minimize the production of EBNA1-derived antigenic peptides presented to the cytotoxic T cells through the MHC class I pathway. The central glycine-alanine repeat (GAr) of EBNA1 plays a critical role in this mechanism of immune evasion as it is able to self-inhibit the translation of its own mRNA in cis. The high level of EBNA1 protein and the efficient T cell response following the infection by an EBV strain encoding a truncated version of EBNA1 in which GAr has been deleted (EBNA1ΔGAr) demonstrates the critical role of GAr in EBNA1 immune evasion. Of note, a polymorphism in the length of GAr exists and, importantly, the effect of GAr is length-dependent as a longer domain displays a stronger inhibitory effect on both mRNA translation and antigen presentation.

The GAr-encoding mRNA sequence is GC rich and forms predicted G-quadruplex (G4) structures that have been implicated in the regulation of EBNA1 synthesis in vitro (Murat et al. *Curr Opin Genet Dev* 2014, 25, 22-29). G4 are particular secondary structures of nucleic acid formed by the stacking of G-quartets which correspond to a planar arrangement of 4 guanines connected by Hoogsteen hydrogen bonds. G4 structures within G-rich DNA or RNA sequences have been implicated in gene regulation where they can affect transcription, alternative splicing and translation. G4 modes of action are still relatively unknown but cellular factors that can interact with these structures are emerging.

GAr-based EBNA1 immune evasion is considered a relevant therapeutic target to treat EBV-related cancers as most tumor cells from EBV-related cancers are infected by EBV whereas, in healthy individuals, the latent infection by EBV is primarily restricted to a specific small pool of memory B cells. Hence, overcoming GAr-based self-inhibition of EBNA1 translation should unveil EBV-carrying tumor cells to cytotoxic T cells without having significant effect on the vast majority of healthy host cells.

A yeast-based (*Saccharomyces cerevisiae*) assay that recapitulates all the aspects of the GAr-based inhibition of translation, including the GAr-length dependency, has been developed, that allowed understanding the mechanisms of GAr-mediated mRNA translation—suppression in cis, as well as the cellular factors involved (Lista et al. *Biotechnol J* 2015, 10, 1670-1681). This assay was successfully used to identify small molecular weight compounds that can stimulate EBNA1 expression both in yeast and mammalian cells and that relieve GAr-based limitation of antigen presentation (Voisset et al. *Dis Model Mech* 2014, 7, 435-444).

Nucleolin (NCL) is a multifunctional DNA/RNA-binding protein widely conserved among eukaryotes. It is involved in RNA metabolism, in particular in rRNA maturation. NCL binds to G-rich sequences in coding and non-coding regions of various mRNA, many of which encode cancer-related proteins, and enhance their translation. In addition, NCL binds to some G4 structures within DNAs and RNAs. For example, it has been recently shown that NCL binds to and stabilizes G4 structures formed within the LTR promoter of HIV, thereby silencing the provirus transcription (Tosoni et al. *Nucleic Acids Res* 2015, 43, 8884-8897). NCL also affects the transcription of c-MYC by binding to and stabilizing G4 present in the promoter of this oncogene and that negatively regulate its activity.

Based on the yeast assay mentioned above, the Inventors have performed a genetic screen to identify host cell genes involved in the GAr-mediated inhibition of translation. This way, the yeast NSR1 gene encoding the orthologue of human NCL was identified, and it was shown that NCL is critically involved in GAr-based limitation of translation and antigen presentation, and thus in EBNA1 immune evasion.

As a result, the NCL-EBNA1 mRNA interaction appears as a relevant therapeutic target for the treatment and/or prevention of EBV-related cancers (see Lista et al., *Nat Commun* 2017, 8, 16043), and it was shown that PhenDC3 is able to prevent NCL from binding to G4 formed in the GAr mRNA sequence, and to stimulate GAr-limited translation and antigen presentation.

There however remains a need for identifying new therapeutic targets, which would disrupt the GAr-based EBNA1 immune evasion of EBV when interacted with by therapeutic agents. Such therapeutic agents, able to interact with these new targets, would thus be useful in the treatment and/or prevention of EBV-related cancers.

SUMMARY OF THE INVENTION

In this context, the Inventors identified novel hydrazone derivatives, in particular cationic N-acylhydrazone derivatives, which were shown to interact with G4 formed in the GAr mRNA sequence involved in the translation of EBNA1, and which yielded positive results in the yeast assay mentioned above.

Therefore, in a first aspect, the present invention relates to a compound of formula (I), or a hydrate or a solvate thereof:

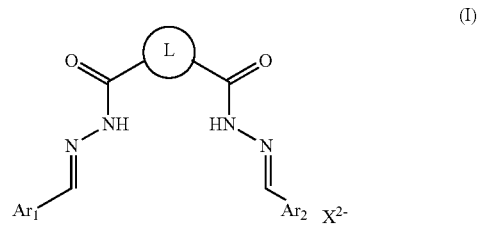

wherein

Ar₁ and Ar₂ may be identical or different and are each independently selected from the group consisting of groups of formula (II) and (III):

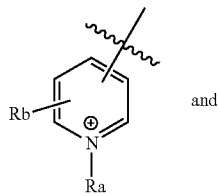
(II)

and

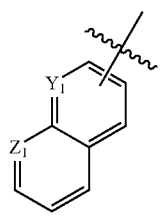
(III)

$R_a$ is $C_1$-$C_6$ alkyl, optionally substituted with a OH group, a O—($C_1$-$C_4$)alkyl group, or a monocyclic or bicyclic 5- to 10-membered aromatic or heteroaromtic group, $R_b$ is a hydrogen atom, a halogen atom, $C_1$-$C_6$ alkyl optionally substituted with a OH group, or a O—($C_1$-$C_4$)alkyl group, $Y_1$ and $Z_1$ are independently CH or $N^+$—$R_c$, provided that al least one of $Y_1$ and $Z_1$ is $N^+$—$R_c^+$ and at least one of $Y_1$ and $Z_1$ is CH, $R_c$ is $C_1$-$C_6$ alkyl, optionally substituted with a OH group, a O—($C_1$-$C_4$)alkyl group, or a monocyclic or bicyclic 5- to 10-membered aromatic or heteroaromtic group, $X^{2-}$ is one or a plurality of pharmaceutically acceptable anion(s), selected so as to obtain an overall electrically neutral salt, L is (A), (B), (C), (D) or (E):

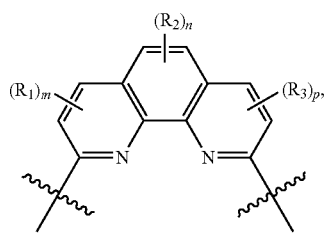
(A)

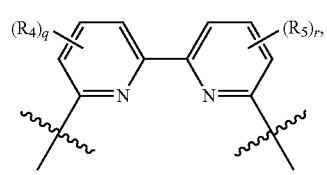
(B)

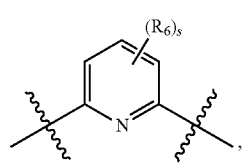
(C)

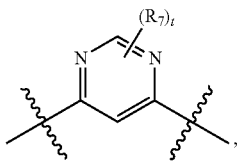
(D)

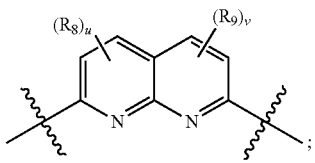
(E)

m, n, p, t, u and v may be identical or different and are each independently an integer selected from 0 to 2;

q, r and s may be identical or different and are each independently an integer selected from 0 to 3;

$R_1$ to $R_9$ may be identical or different and are each independently a halogen atom, a $C_1$-$C_6$ alkyl group, a $C_3$-$C_8$ cycloalkyl group, a O($C_1$-$C_6$)alkyl group, a $NR_{10}R_{11}$ group, a $C_2$-$C_6$ alkenyl group, a $C_5$-$C_8$ cycloalkenyl group, said $C_1$-$C_6$ alkyl group, $C_3$-$C_8$ cycloalkyl group, O($C_1$-$C_6$) alkyl group, $C_2$-$C_6$ alkenyl group, or $C_5$-$C_8$ cycloalkenyl group being optionally substituted with one to three halogen atoms, a OH group, a O—($C_1$-$C_6$)alkyl group, a NH—($C_1$-$C_6$)alkyl group or a NHC(O)—R';

$R_{10}$ and $R_{11}$ may be identical or different and are each independently:
  a hydrogen atom,
  a $C_1$-$C_6$ alkyl group optionally substituted with a OH group, a O—($C_1$-$C_6$)alkyl group, a NH—($C_1$-$C_6$)alkyl group or a NHC(O)R'— group;
  or $NR_{10}R_{11}$, taken together, form a 3- to 8-membered heterocycloalkyl or 5- to 8-membered heterocycloalkenyl;

R' is a ($C_1$-$C_6$)alkyl group optionally substituted with a $C_5$-$C_{10}$ aryl group, wherein said $C_5$-$C_{10}$ aryl group is optionally substituted with a halogen atom, a $C_1$-$C_6$ alkyl group, a O($C_1$-$C_6$)alkyl group, a $C_2$-$C_8$ alkenyl group, a $C_5$-$C_8$ cycloalkenyl group, a 3- to 8-membered heterocycloalkyl, a 5- to 8-membered heterocycloalkenyl, a N(($C_1$-$C_6$)alkyl)₂ group or a N(($C_1$-$C_6$)haloalkyl)₂ group.

In a preferred embodiment, L is (A), (C) or (E):

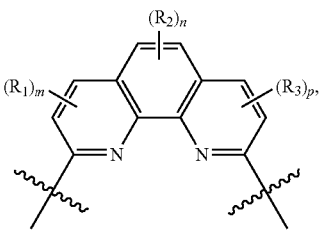
(A)

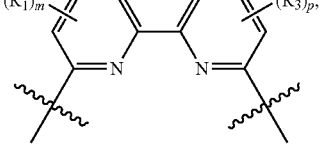
(C)

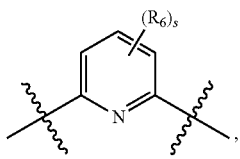

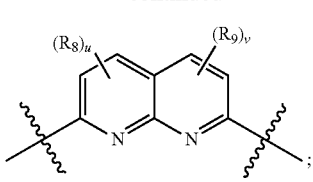

provided that $Ar_1$ and $Ar_2$ are not groups of formula (II) when L is (C) or (E), m, n, p, u and v may be identical or different and are each independently an integer selected from 0 to 2;

s is an integer selected from 0 to 3;

$R_1$, $R_2$, $R_3$, $R_6$, $R_8$ and $R_9$ may be identical or different and are each independently a halogen atom, a $C_1$-$C_6$ alkyl group, a $C_3$-$C_8$ cycloalkyl group, a $O(C_1$-$C_6)$alkyl group, a $NR_{10}R_{11}$ group, a $C_2$-$C_6$ alkenyl group, a $C_5$-$C_8$ cycloalkenyl group said $C_1$-$C_6$ alkyl group, $C_3$-$C_8$ cycloalkyl group, $O(C_1$-$C_6)$alkyl group, $C_2$-$C_6$ alkenyl group, or $C_5$-$C_8$ cycloalkenyl group being optionally substituted with one to three halogen atoms, a OH group, a O—$(C_1$-$C_6)$alkyl group, a NH—$(C_1$-$C_6)$alkyl group or a NHC(O)—R';

$R_{10}$ and $R_{11}$ may be identical or different and are each independently:
- a hydrogen atom,
- a $C_1$-$C_6$ alkyl group optionally substituted with a OH group, a —$(C_1$-$C_6)$alkyl group, a NH—$(C_1$-$C_6)$alkyl group or a NHC(O)—R', or $NR_{10}R_{11}$, taken together, form a 3- to 8-membered heterocycloalkyl or 5- to 8-membered heterocycloalkenyl, R' is a $(C_5$-$C_6)$alkyl group optionally substituted with a $C_5$-$C_{10}$ aryl group, wherein said $C_5$-$C_{10}$ aryl group is optionally substituted with a halogen atom, a $C_1$-$C_8$ alkyl group, a $O(C_1$-$C_6)$alkyl group, a $C_2$-$C_8$ alkenyl group, a $C_5$-$C_8$ cycloalkenyl group, a 3- to 8-membered heterocycloalkyl, a 5- to 8-membered heterocycloalkenyl, a $N((C_1$-$C_6)$alkyl$)_2$ group or a $N((C_1$-$C_6)$haloalkyl$)_2$ group.

Advantageously, compounds of formula (I) according to the present invention do not include any metal complex or coordination compound.

For the purpose of the invention, the term □pharmaceutically acceptable□ is intended to mean what is useful to the preparation of a pharmaceutical composition, and what is generally safe and non-toxic, for a pharmaceutical use.

The term □pharmaceutically acceptable salt□ is intended to mean, in the framework of the present invention, a salt of a compound which is pharmaceutically acceptable, as defined above, and which possesses the pharmacological activity of the corresponding compound.

In another aspect, the present invention relates to a composition comprising:
- as active ingredient, the compound of formula (I) as described above or below, or a hydrate or a solvate thereof, and optionally another therapeutic agent selected from antibiotics, anticancer agents, steroidal and non-steroidal anti-inflammatory drugs, and
- a pharmaceutically acceptable excipient.

In another aspect, the present invention relates to a kit comprising at least:
- a first composition comprising the compound of formula (I) as defined above or below, and a pharmaceutically acceptable excipient, and
- a second composition comprising another therapeutic agent preferably selected from antibiotics, anticancer agents, steroidal and non-steroidal anti-inflammatory drugs, especially as a combination product for simultaneous, staggered or sequential use.

In another aspect, the present invention relates to the compounds or the compositions of the invention or the kit of the invention for use as drug, in particular for treating an Epstein-Barr-Virus (EBV)-related cancer.

In another aspect, the present invention relates to the use of a compound of formula (I) as defined above or below, or a hydrate or a solvate thereof, or the composition or kit of the invention, for the manufacture of a medicament for preventing or treating an EBV-related cancer.

In another aspect, the present invention relates to a method for preventing or treating an EBV-related cancer comprising administering to a patient in need thereof a therapeutically effective amount of a compound of formula (I) as defined above or below, or a hydrate or a solvate thereof, or the composition or the kit of the invention.

In another aspect, the present invention relates to a process for preparing the compounds of formula (I) as defined above or below.

DETAILED DESCRIPTION

Compounds of Formula (I)

L

Preferably, L is (A), (C), (D) or (E), more preferably L is (A), (C) or (E), even more preferably L is (A) or (C).

In a particular embodiment, L is (C) and s is 0, or L is (A), and
- m and p are 0, and n is 0 or 1, or
- m and n are 0, and p is 0 or 1, or
- n is 0, and m and p are identical and are 0 or 1, or
- m, n and p are 0.

In another particular embodiment,
- L is (B) and q and r are 0, or
- L is (D) and t is 0, or
- L is (E) and u and v are 0.

In a particular embodiment, $R_1$ to $R_9$ may be identical or different and are each independently a halogen atom, a $C_1$-$C_6$ alkyl group, a $O(C_1$-$C_6)$alkyl group, or a $NR_{10}R_{11}$ group, said $C_1$-$C_6$ alkyl group or $O(C_1$-$C_6)$alkyl group, group being optionally substituted with one of two halogen atoms, a OH group, a O—$(C_1$-$C_6)$alkyl group, a NH—$(C_1$-$C_6)$alkyl group or a NHC(O)—R' group;

$R_{10}$ and $R_{11}$ may be identical or different and are each independently:
- a hydrogen atom,
- a $C_1$-$C_5$ alkyl group optionally substituted with a OH group, a O—$(C_1$-$C_6)$alkyl group, a NH—$(C_1$-$C_6)$alkyl group or a NHC(O)R'— group;

or $NR_{10}R_{11}$, taken together, form a 3- to 8-membered heterocycloalkyl;

R' is as defined above or below.

Advantageously, R' is a $(C_1$-$C_6)$alkyl group optionally substituted with a 5- to 10-membered aryl group, wherein said 5- to 10-membered aryl group is optionally substituted with a halogen atom, a $C_1$-$C_6$ alkyl group, a $O(C_1$-$C_6)$alkyl group, a 3- to 8-membered heterocycloalkyl, a 5- to 8-membered heterocycloalkenyl, a $N((C_1$-$C_6)$alkyl$)_2$ group or a $N((C_1$-$C_6)$haloalkyl$)_2$ group.

In a particular embodiment, $R_1$ to $R_9$ may be identical or different and are each independently a halogen atom, a $C_1$-$C_6$ alkyl group, a $C_3$-$C_8$ cycloalkyl group, a $O(C_1$-$C_6)$ alkyl group, a $NR_{10}R_{11}$ group, a $C_2$-$C_6$ alkenyl group, a $C_5$-$C_8$ cycloalkenyl group; $R_{10}$ and $R_{11}$ may be identical or different and are each independently:

a hydrogen atom,
a $C_1$-$C_6$ alkyl group optionally substituted with a OH group, a O—($C_1$-$C_6$)alkyl group, a NH—($C_1$-$C_6$)alkyl group,
or $NR_{10}R_{11}$, taken together, form a 3- to 8-membered heterocycloalkyl or 5- to 8-membered heterocycloalkenyl.

$Ar_1$, $Ar_2$

In a particular embodiment, $R_a$ is $C_1$-$C_6$ alkyl, optionally substituted with a OH group, a O—($C_1$-$C_4$)alkyl group or a monocyclic 5- or 6-membered aromatic or heteroaromtic group, such as a phenyl or a pyridine group. Advantageously, $R_a$ is $C_1$-$C_4$ alkyl, optionally substituted with a OH group, a O—($C_1$-$C_4$)alkyl group or a monocyclic 5- or 6-membered aromatic or heteroaromtic group, such as a phenyl or a pyridine group. Preferably, $R_a$ is $C_1$-$C_4$ alkyl, optionally substituted with a monocyclic 5- or 6-membered aromatic or heteroaromtic group, such as a phenyl or a pyridine group. Most preferably, $R_a$ is an ethyl, a methyl group or a benzyl group.

In a particular embodiment, $R_b$ is a hydrogen atom, a halogen atom, $C_1$-$C_6$ alkyl optionally substituted with a OH group, or a O—($C_1$-$C_4$)alkyl group, preferably $R_b$ is a hydrogen atom or a halogen atom, most preferably $R_b$ is a hydrogen atom.

In a particular embodiment, $R_c$ is $C_1$-$C_6$ alkyl, optionally substituted with a OH group, a O—($C_1$-$C_4$)alkyl group or a monocyclic 5- or 6-membered aromatic or heteroaromtic group, such as a phenyl or a pyridine group. Advantageously, $R_c$ is $C_1$-$C_4$ alkyl, optionally substituted with a OH group, a O—($C_1$-$C_4$)alkyl group or a monocyclic 5- or 6-membered aromatic or heteroaromtic group, such as a phenyl or a pyridine group.

Preferably, $R_c$ is $C_1$-$C_4$ alkyl, optionally substituted with a monocyclic 5- or 6-membered aromatic or heteroaromtic group, such as a phenyl or a pyridine group. Most preferably, $R_c$ is an ethyl, a methyl group or a benzyl group.

In a particular embodiment, $Ar_1$ and $Ar_2$ may be identical or different and are each independently selected from the group consisting of groups of formula (II'), (III') and (III''):

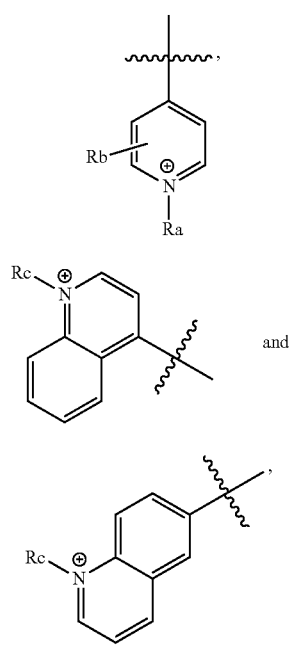

with $R_a$, $R_b$ and $R_c$ as defined above or below.

In a particular embodiment, $Ar_1$ and/or $Ar_2$ are of formula (II) or (II'), $R_a$ is a linear $C_1$-$C_4$ alkyl optionally substituted with a phenyl group (preferably an ethyl, a methyl group or a benzyl group), and $R_b$ is a hydrogen or halogen atom, preferably a hydrogen atom. Preferably, in this embodiment, $Ar_1$ and/or (advantageously and) $Ar_2$ are of formula (II'), $R_a$ is a ethyl, a methyl group or a benzyl group and $R_b$ is a hydrogen atom.

In another preferred embodiment, $Ar_1$ and/or $Ar_2$ are of formula (III') or (III''), and $R_c$ is a linear $C_1$-$C_4$ alkyl optionally substituted with a phenyl group, preferably an ethyl, a methyl group or a benzyl group. Preferably, in this embodiment, $Ar_1$ and/or (advantageously and) $Ar_2$ are of formula (III'), and $R_c$ is an ethyl, a methyl group or a benzyl group.

$X^{2-}$

As stated above, $X^{2-}$ is one or a plurality of pharmaceutically acceptable anion(s), selected so as to obtain an overall electrically neutral (pharmaceutically acceptable) salt.

The nature of the anion may vary, provided that it is pharmaceutically acceptable, and yields a pharmaceutically acceptable salt. Suitable pharmaceutically acceptable anions may be prepared from the corresponding base of an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. The salts of the compounds of formula (I) may be prepared by conventional methods from the corresponding compound, for example, using an anion-exchange resin, pre-treated with the appropriate acid, optionally in the form of a metallic or alkaline or alkaline earth base, with any of the compounds of the invention.

Advantageously, according to the present invention, $X^{2-}$ is not a metallic ion. Compounds of the present invention do not include metal complexes or coordination compounds.

Typically, $X^{2-}$ represents one or a plurality (generally 2) anion(s) as defined above with two negative charges. Advantageously, $X^{2-}$ represents 2 anions selected from the group consisting of a halogenide, a carboxylate, a $C_1$-$C_6$alkylsulfonate, a $C_1$-$C_6$haloalkylsulfonate and an alkylarylsulfonate, preferably a halogenide, a methanesulfonate, a trifluoromethanesulfonate or a tosylate.

For instance, $X^{2-}$ represents 2 anions selected from the group consisting of $Cl^-$, $Br^-$, $I^-$, and $CF_3SO_3^-$, such as $Br^-$, $I^-$, and $CF_3SO_3^-$.

Combinations

When L is (C) or (D), then $Ar_1$ and $Ar_2$ are identical or different and are advantageously of formula (III).

When $Ar_1$ and/or $Ar_2$ is of formula (II), then L is preferably of formula (A), (B), or (E), more preferably of formula (A) or (E). For instance, when $Ar_1$ and/or $Ar_2$ is of formula (II), L is of formula (A).

In a preferred embodiment, the compound of formula (I) is characterized in that: $Ar_1$ and $Ar_2$ are identical and selected from the group consisting of groups of formula (II'), (III') and (III☐), $R_a$ is $C_1$-$C_6$ alkyl, optionally substituted with a OH group, a O—($C_1$-$C_4$)alkyl group or a monocyclic or bicyclic 5- to 10-membered aromatic or heteroaromatic group, preferably $R_a$ is ethyl, methyl or benzyl, $R_b$ is a hydrogen atom, $Y_1$ and $Z_1$ are independently CH or $NR_c^+$, provided that al least one of $Y_1$ and $Z_1$ is $NR_c^+$ and at least one of $Y_1$ and $Z_1$ is CH, $R_c$ is $C_1$-$C_6$ alkyl, optionally substituted with a OH group, a O—($C_1$-$C_4$)alkyl group, or a monocyclic or bicyclic 5- to 10-membered aromatic or heteroaromtic group, preferably $R_c$ is ethyl, methyl or benzyl, $X^{2-}$ is one or a plurality of pharmaceutically acceptable anion(s), selected so as to obtain an overall electrically neutral salt, preferably 2 I⁻ or 2 Br⁻, L is (A), (C), (D) or (E), m, n, p, t, u and v may be identical or different and are each independently an integer selected from 0 to 2;

s is an integer selected from 0 to 3;

$R_1$ to $R_9$ may be identical or different and are each independently a halogen atom, a $C_1$-$C_6$ alkyl group, a $C_3$-$C_8$ cycloalkyl group, a O($C_1$-$C_6$)alkyl group, a $NR_{10}R_{11}$ group, a $C_2$-$C_6$ alkenyl group, a $C_5$-$C_8$ cycloalkenyl group;

$R_{10}$ and $R_{11}$ may be identical or different and are each independently:
  a hydrogen atom,
  a $C_1$-$C_6$ alkyl group optionally substituted with a OH group, a O—($C_1$-$C_6$)alkyl group, a NH—($C_1$-$C_6$)alkyl group, or $NR_{10}R_{11}$, taken together, form a 3- to 8-membered heterocycloalkyl or 5- to 8-membered heterocycloalkenyl.

In this preferred embodiment, $Ar_1$ and $Ar_2$ are preferably identical, and of formula (II'), (III') or (III☐).

In this preferred embodiment, advantageously, L is (C) and s is 0, or L is (A), and
  m and p are 0, and n is 0 or 1, or
  m and n are 0, and p is 0 or 1, or
  n is 0, and m and p are identical and are 0 or 1, or
  m, n and p are 0.

Preferably, in this embodiment, m, n, p, s, t, u and v are all 0.

In another preferred embodiment, the compound of formula (I) is characterized in that: $Ar_1$ and $Ar_2$ may be identical or different and are each independently selected from the group consisting of groups of formula (II) and (III), $R_a$ is $C_1$-$C_6$ alkyl, optionally substituted with a OH group, a O—($C_1$-$C_4$)alkyl group or a monocyclic or bicyclic 5- to 10-membered aromatic or heteroaromatic group, preferably $R_a$ is a linear $C_1$-$C_4$ alkyl optionally substituted with a phenyl group, more preferably $R_a$ is an ethyl, a methyl or a benzyl group, $R_b$ is a hydrogen atom, a halogen atom, $C_1$-$C_6$ alkyl optionally substituted with a OH group, or a O—($C_1$-$C_4$)alkyl group, preferably $R_b$ is a hydrogen or halogen atom, more preferably $R_b$ is a hydrogen atom, $Y_1$ and $Z_1$ are independently CH or N⁺—$R_c$, provided that al least one of $Y_1$ and $Z_1$ is N⁺—$R_c^+$ and at least one of $Y_1$ and $Z_1$ is CH, $R_c$ is $C_1$-$C_6$ alkyl, optionally substituted with a OH group, a O—($C_1$-$C_4$)alkyl group, or a monocyclic or bicyclic 5- to 10-membered aromatic or heteroaromtic group, preferably $R_c$ a linear $C_1$-$C_4$ alkyl optionally substituted with a phenyl group, more preferably $R_c$ is an ethyl, a methyl or a benzyl group, $X^{2-}$ is one or a plurality of pharmaceutically acceptable anion(s), selected so as to obtain an overall electrically neutral salt, preferably $X^{2-}$ represents two anions selected from the group consisting of a halogenide, a carboxylate, a $C_1$-$C_6$alkylsulfonate, a $C_1$-$C_6$haloalkylsulfonate and an alkylarylsulfonate, more preferably $X^{2-}$ is 2 I⁻ or 2 Br⁻, L is (A), (C) or (E), provided that $Ar_1$ and $Ar_2$ are not groups of formula (II) when L is (C) or (E), m, n, p, u and v may be identical or different and are each independently an integer selected from 0 to 2;

s is an integer selected from 0 to 3;

$R_1$, $R_2$, $R_3$, $R_6$, $R_8$ and $R_9$ may be identical or different and are each independently a halogen atom, a $C_1$-$C_6$ alkyl group, a $C_3$-$C_8$ cycloalkyl group, a O($C_1$-$C_6$)alkyl group, a $NR_{10}R_{11}$ group, a $C_2$-$C_8$ alkenyl group, a $C_5$-$C_8$ cycloalkenyl group said $C_1$-$C_6$ alkyl group, $C_3$-$C_8$ cycloalkyl group, O($C_1$-$C_6$)alkyl group, $C_2$-$C_6$ alkenyl group, or $C_5$-$C_8$ cycloalkenyl group being optionally substituted with one to three halogen atoms, a OH group, a O—($C_1$-$C_6$)alkyl group, a NH—($C_1$-$C_6$)alkyl group or a NHC(O)—R';

$R_{10}$ and $R_{11}$ may be identical or different and are each independently:
  a hydrogen atom,
  a $C_1$-$C_6$ alkyl group optionally substituted with a OH group, a O—($C_1$-$C_6$)alkyl group, a NH—($C_1$-$C_6$)alkyl group or NHC(O)—R', or $NR_{10}R_{11}$, taken together, form a 3- to 8-membered heterocycloalkyl or 5- to 8-membered heterocycloalkenyl, R' is a ($C_1$-$C_5$)alkyl group optionally substituted with a $C_5$-$C_{10}$ aryl group, wherein said $C_5$-$C_{10}$ aryl group is optionally substituted with a halogen atom, a $C_1$-$C_6$ alkyl group, a O($C_1$-$C_6$)alkyl group, a $C_2$-$C_6$ alkenyl group, a $C_5$-$C_8$cycloalkenyl group, a 3- to 8-membered heterocycloalkyl, a 5- to 8-membered heterocycloalkenyl, a N(($C_1$-$C_6$)alkyl)$_2$ group or a N(($C_1$-$C_6$)haloalkyl)$_2$ group.

Advantageously, $Ar_1$ and $Ar_2$ may be identical or different and are each independently selected from the group consisting of formula (II), (III') and (III☐).

In this preferred embodiment, advantageously L is (C), s is 0 and $Ar_1$ and $Ar_2$ are preferably identical, and of formula (III), preferably of formula (III') or (III☐), or L is (A), $Ar_1$ and $Ar_2$ are preferably identical, and of formula (II) or (III), preferably of formula (I'), (III') or (III☐) and m and p are 0, and n is 0 or 1, or
  m and n are 0, and p is 0 or 1, or
  n is 0, and m and are identical and are 0 or 1, or
  m, n and p are 0.

Preferably, in this embodiment, m, n, p, s, t, u and v are all 0.

Exemplary cationic compounds of formula (I) are as follows:

| No | L | $Ar_1$ and $Ar_2$ are identical and are both |
|----|---|---------------------------------------------|
| 1a | 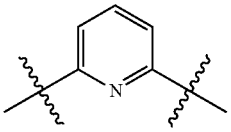 [SMILES: *c1cccc(*)n1] | 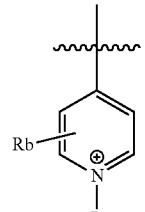<br>with $R_b$ being H and $R_a$ being methyl |

| No | L | Ar₁ and Ar₂ are identical and are both |
|---|---|---|
| 1b | pyridine (2,6-linked) | pyridinium with $R_b$ being H and $R_a$ being ethyl |
| 1c | pyridine (2,6-linked) | pyridinium with $R_b$ being H and $R_a$ being benzyl |
| 2a | pyridine (2,6-linked) | quinolinium with $R_c$ being methyl |
| 2b | pyridine (2,6-linked) | quinolinium with $R_c$ being ethyl |
| 2c | pyridine (2,6-linked) | quinolinium with $R_c$ being benzyl |
| 3a | pyridine (2,6-linked) | quinolinium (6-linked) with $R_c$ being methyl |
| 3b | pyridine (2,6-linked) | quinolinium (6-linked) with $R_c$ being ethyl |
| 3c | pyridine (2,6-linked) | quinolinium (6-linked) with $R_c$ being benzyl |
| 4a | pyrimidine (4,6-linked) | pyridinium with $R_b$ being H and $R_a$ being methyl |
| 4b | pyrimidine (4,6-linked) | pyridinium with $R_b$ being H and $R_a$ being ethyl |
| 4c | pyrimidine (4,6-linked) | pyridinium with $R_b$ being H and $R_a$ being benzyl |
| 5a | pyrimidine (4,6-linked) | quinolinium with $R_c$ being methyl |

| No | L | Ar₁ and Ar₂ are identical and are both |
|---|---|---|
| 5b | pyrimidine-4,6-diyl | quinolinium-4-yl with R_c being ethyl |
| 5c | pyrimidine-4,6-diyl | quinolinium-4-yl with R_c being benzyl |
| 6a | pyrimidine-4,6-diyl | quinolinium-6-yl with R_c being methyl |
| 6b | pyrimidine-4,6-diyl | quinolinium-6-yl with R_c being ethyl |
| 6c | pyrimidine-4,6-diyl | quinolinium-6-yl with R_c being benzyl |
| 7a | 1,8-naphthyridine-2,7-diyl | pyridinium-4-yl with R_b being H and R_a being methyl |
| 7b | 1,8-naphthyridine-2,7-diyl | pyridinium-4-yl with R_b being H and R_a being ethyl |
| 7c | 1,8-naphthyridine-2,7-diyl | pyridinium-4-yl with R_b being H and R_a being benzyl |
| 8a | 1,8-naphthyridine-2,7-diyl | quinolinium-4-yl with R_c being methyl |
| 8b | 1,8-naphthyridine-2,7-diyl | quinolinium-4-yl with R_c being ethyl |
| 8c | 1,8-naphthyridine-2,7-diyl | quinolinium-4-yl with R_c being benzyl |
| 9a | 1,8-naphthyridine-2,7-diyl | quinolinium-6-yl with R_c being methyl |

| No | L | Ar₁ and Ar₂ are identical and are both |
|---|---|---|
| 9b | [1,8-naphthyridine-2,7-diyl] | quinolinium with R_c being ethyl |
| 9c | [1,8-naphthyridine-2,7-diyl] | quinolinium with R_c being benzyl |
| 10a | [1,10-phenanthroline-2,9-diyl] | pyridinium with R_b being H and R_a being methyl |
| 10b | [1,10-phenanthroline-2,9-diyl] | pyridinium with R_b being H and R_a being ethyl |
| 10c | [1,10-phenanthroline-2,9-diyl] | pyridinium with R_b being H and R_a being benzyl |
| 11a | [1,10-phenanthroline-2,9-diyl] | quinolinium with R_c being methyl |
| 11b | [1,10-phenanthroline-2,9-diyl] | quinolinium with R_c being ethyl |
| 11c | [1,10-phenanthroline-2,9-diyl] | quinolinium with R_c being benzyl |
| 12a | [1,10-phenanthroline-2,9-diyl] | quinolinium with R_c being methyl |
| 12b | [1,10-phenanthroline-2,9-diyl] | quinolinium with R_c being ethyl |
| 12c | [1,10-phenanthroline-2,9-diyl] | quinolinium with R_c being benzyl | with $X^{2-}$ as defined above, especially representing 2 anions selected from the group consisting of a halogenide, a carboxylate, a $C_1$-$C_6$alkylsulfonate, a $C_1$-$C_6$haloalkylsulfonate and an alkylarylsulfonate, preferably a halogenide, a methanesulfonate, a trifluoromethanesulfonate or a tosylate for instance, 2 anions selected from the group consisting of $Cl^-$, $Br^-$, $I^-$, and $CHF_3SO_3^-$, such as $Br^-$, $I^-$, and $CHF_3SO_3^-$, preferably $Br^-$ or $I^-$.

The preferred exemplary cationic compounds of formula (I) are as follows:

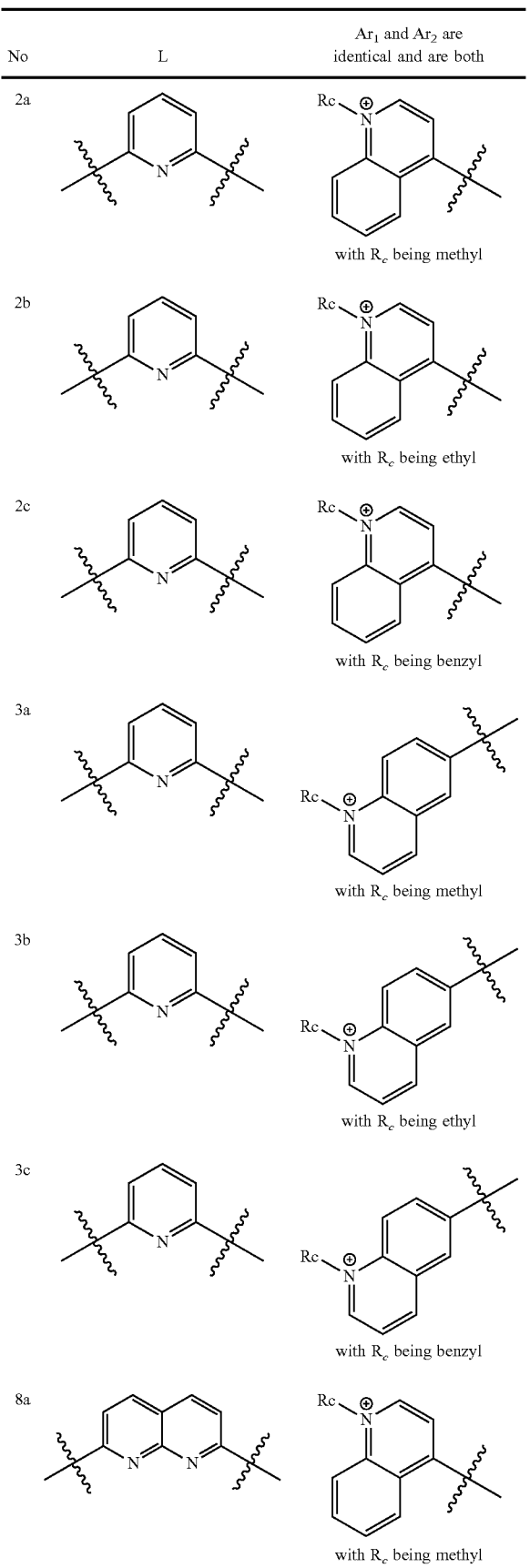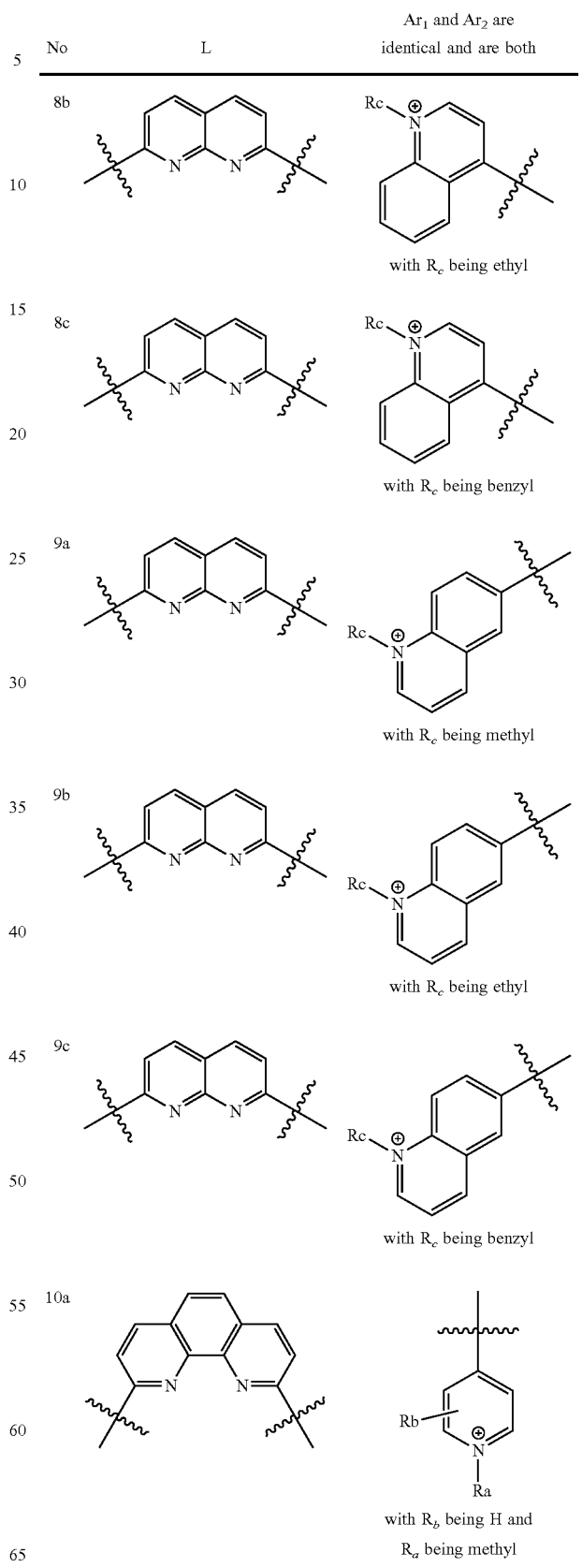

-continued

| No | L | Ar₁ and Ar₂ are identical and are both |
|---|---|---|
| 10b | (1,10-phenanthroline-2,9-diyl) | 4-pyridinium, with $R_b$ being H and $R_a$ being ethyl |
| 10c | (1,10-phenanthroline-2,9-diyl) | 4-pyridinium, with $R_b$ being H and $R_a$ being benzyl |
| 11a | (1,10-phenanthroline-2,9-diyl) | 4-quinolinium, with $R_c$ being methyl |
| 11b | (1,10-phenanthroline-2,9-diyl) | 4-quinolinium, with $R_c$ being ethyl |
| 11c | (1,10-phenanthroline-2,9-diyl) | 4-quinolinium, with $R_c$ being benzyl |
| 12a | (1,10-phenanthroline-2,9-diyl) | 6-quinolinium, with $R_c$ being methyl |
| 12b | (1,10-phenanthroline-2,9-diyl) | 6-quinolinium, with $R_c$ being ethyl |
| 12c | (1,10-phenanthroline-2,9-diyl) | 6-quinolinium, with $R_c$ being benzyl | with $X^{2-}$ as defined above, especially representing 2 anions selected from the group consisting of a halogenide, a carboxylate, a $C_1$-$C_6$alkylsulfonate, a $C_1$-$C_6$haloalkylsulfonate and an alkylarylsulfonate, preferably a halogenide, a methanesulfonate, a trifluoromethanesulfonate or a tosylate for instance, 2 anions selected from the group consisting of Cl⁻, Br⁻, I⁻, and $CHF_3SO_3^-$, such as Br⁻, I⁻, and $CHF_3SO_3^-$, preferably Br⁻ or I⁻.

In an advantageous embodiment, the compound is compound 2a, 2b, 2c, 3a, 3b, 3c, 5a, 5b, 5c, 6a, 6b, 6c, 7a, 7b, 7c, 8a, 8b, 8c, 9a, 9b, 9c, 10a, 10b, 10c, 11a, 11b, 11c, 12a, 12b, 12c, such as compound 2a, 2b, 2c, 3a, 3b, 3c, 7a, 7b, 7c, 8a, 8b, 8c, 9a, 9b, 9c, 10a, 10b, 10c, 11a, 11b, 11c, 12a, 12b, 12c, preferably compound 2a, 2b, 2c, 3a, 3b, 3c, 8a, 8b, 8c, 9a, 9b, 9c, 10a, 10b, 10c, 11a, 11b, 11c, 12a, 12b, 12c with $X^{2-}$ as defined above, especially representing 2 anions selected from the group consisting of a halogenide, a carboxylate, a $C_1$-$C_6$alkylsulfonate, a $C_1$-$C_6$haloalkylsulfonate and an alkylarylsulfonate, preferably a halogenide, a methanesulfonate, a trifluoromethanesulfonate or a tosylate for instance, 2 anions selected from the group consisting of Br⁻ or I⁻.

Advantageously, the compound of the invention is compound 2a, 2c, 3b, 3c, 8a, 8c, 9b, 9c, 10a, 11a, 11c, 12b, 12c, in particular it is compound 2a, 2c, 10a, 11a, 11c with $X^{2-}$ representing 2 anions selected from the group consisting of Br⁻ or I⁻. Advantageously, the compound of the invention is:

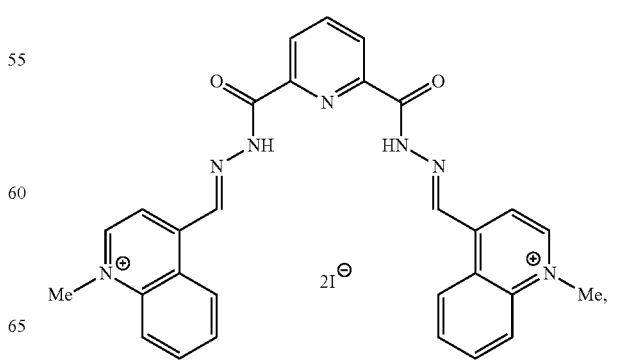

(2a)

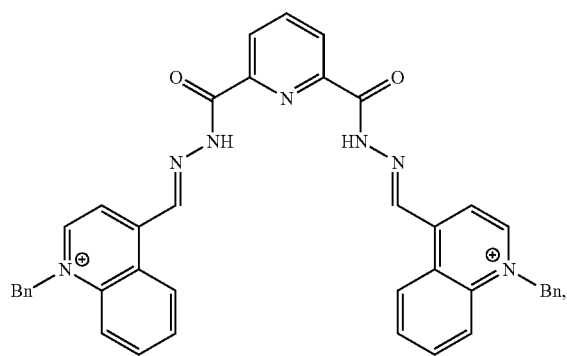
(2c)
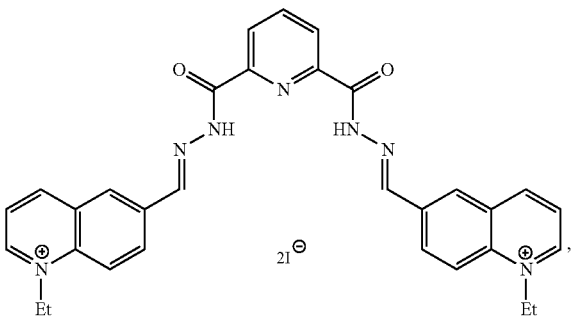
(3b)
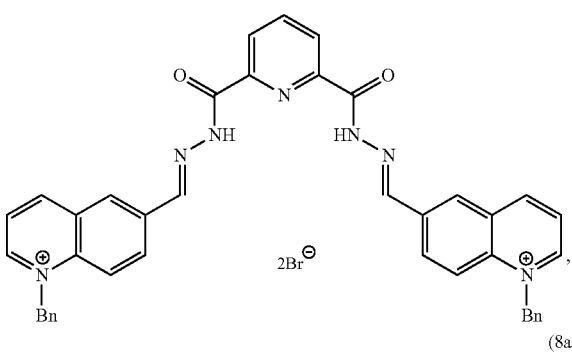
(3c)
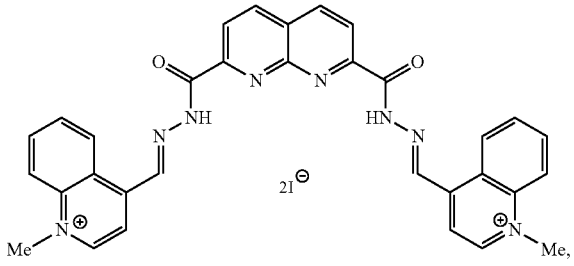
(8a)
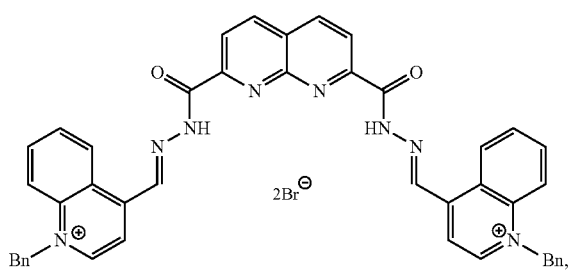
(8c)
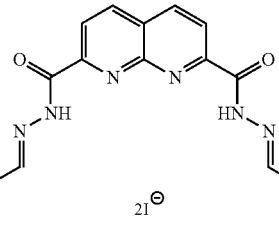
(9b)
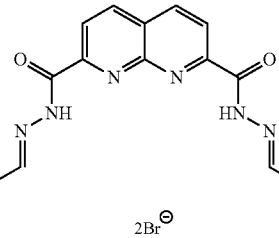
(9c)
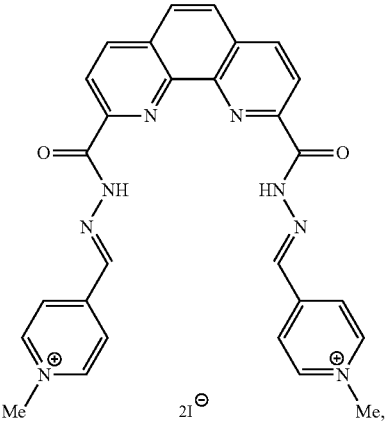
(10a)
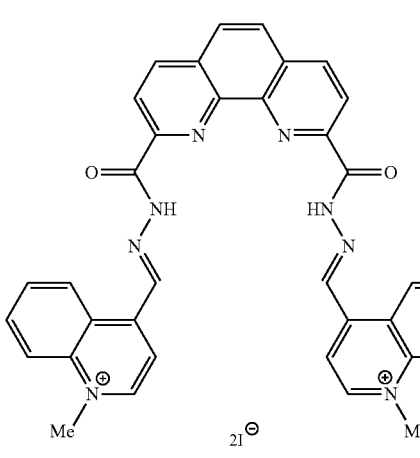
(11a)

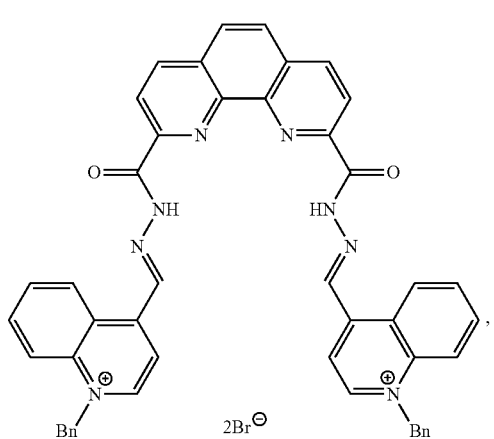
(11c)

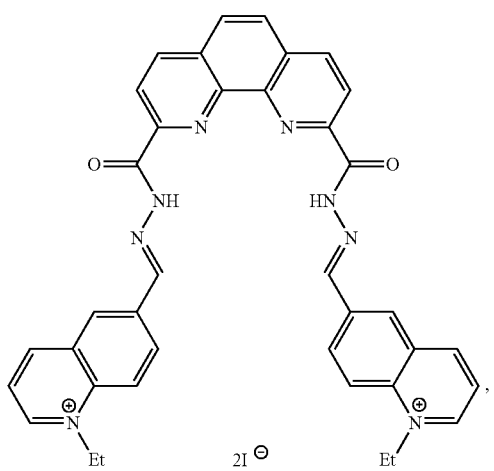
(12b)

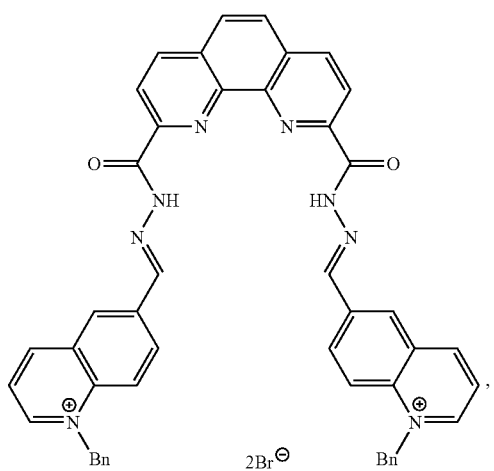
(12c)

preferably 2a, 2c, 10a, 11a, and 11c, most preferably 2a.

Miscellaneous

The present invention encompasses only stable compounds.

The compounds of formula (I) as described above may exist in tautomeric, diastereomeric or enantiomeric forms. The present invention contemplates all such compounds, including cis- and trans-diastereomers, E- and Z-stereomers, R- and S-enantiomers, diastereomers, d-isomers, l-isomers, the racemic mixtures thereof and other mixtures thereof. Pharmaceutically acceptable salts of such tautomeric, diastereomeric or enantiomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, where the compounds described contain one or more stereocenters, the present invention includes R, S, and mixtures of R and S forms for each stereocenter present.

Process for Preparing the Compounds of Formula (I)

A process for preparing the compounds of formula (I) comprises the following successive steps:

a) Condensing $NH_2NH_2.H_2O$ (hydrazine hydrate) with an ester of formula (IV),

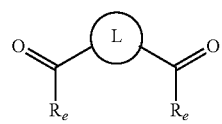
(IV)

wherein L is as defined above, and $R_e$ is a $O(C_1$-$C_6)$alkyl group, said $C_1$-$C_6$ alkyl being optionally substituted with a OH group, a $O$—$(C_1$-$C_4)$alkyl group or a monocyclic or bicyclic 5- to 10-membered aromatic or heteroaromtic group,

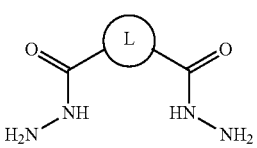
(V)

to obtain hydrazone (V), with L as defined above, b) Condensing the compound of formula (V) with an aldehyde of formula $Ar_1'$—CHO
and/or an aldehyde of formula $Ar_2'$—CHO, $Ar_1'$ and $Ar_2'$ being identical or different and each independently selected from the group consisting of groups of formula (IIa) and (IIIa):

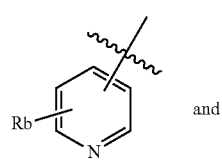
and
(IIa)

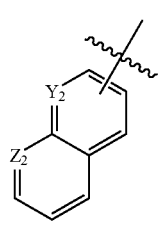
(IIIa)

with $R_b$ as defined above, $Y_2$ and $Z_2$ being independently CH or N, provided that al least one of $Y_2$ and $Z_2$ is N and at least one of $Y_2$ and $Z_2$ is CH, to obtain Intermediate (VI),

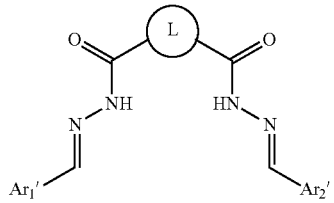

(VI)

with L, $Ar_1'$ and $Ar_2'$ as defined above, and c) Alkylating Intermediate (VI) with an alkylating agent of formula $R_d$—Z, wherein Z is a leaving group, preferably a halogen atom such as Br or I, and $R_d$ is a $C_1$-$C_6$ alkyl, optionally substituted with a OH group, a O—($C_1$-$C_4$)alkyl group or a monocyclic or bicyclic 5- to 10-membered aromatic or heteroaromtic group, to obtain the compound of formula (I) as defined above.

$R_e$ is advantageously a O($C_1$-$C_4$)alkyl group, optionally substituted with a OH, $OCH_3$ or phenyl group, such as a methyl, an ethyl or a benzyl group, preferably a methyl or ethyl group.

Compounds of formula (IV) are commercial or easily accessible to the one of skill in the art. They may be prepared by methods known in the art, as described for instance in European patent application no 17305588.0, filed on 19 May 2017 (see for instance page 6 and examples). In particular, compounds of formula (IV) wherein m, n, p, q, r, s, t, u, or v is not 0 may easily be obtained from the corresponding dimethyl heteroarene, oxidized into the corresponding dicarboxylic acid and subsequently converted into a corresponding dimethyl ester of formula (IV).

Step a) is preferably performed under heating in a solvent such as an alcohol, preferably ethanol.

Step b) is preferably performed under heating in a solvent such as an alcohol, preferably ethanol.

Step c) is preferably performed under heating in a polar solvent such as a polar aprotic solvent, in particular dimethylformamide (DMF).

In particular, compound 2a is obtained as follows:

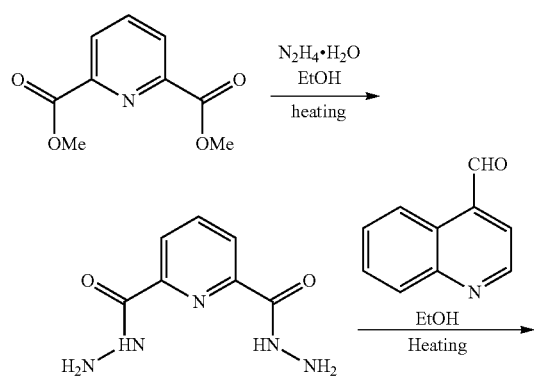

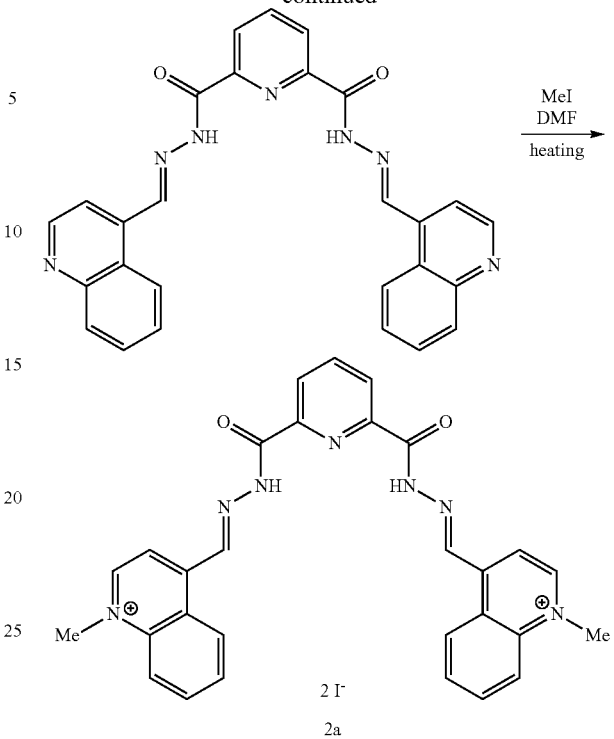

2a

Pharmaceutical Compositions

The pharmaceutically acceptable excipient is selected, according to the dosage form and mode of administration desired, from the typical excipients known to persons skilled in the art.

The pharmaceutical compositions according to the invention can be administered parenterally (such as intravenously or intradermally), topically, orally or rectally.

The term □parenteral□ as used herein includes subcutaneous, intravenous, intramuscular, intravesical or infusion techniques. Preferably, the term □parenteral□ refers to infusion techniques.

For therapeutic purposes, formulations for parenteral administration may be in the form of aqueous or non-aqueous isotonic sterile injection solutions or suspensions.

Injectable preparations, for example, sterile injectable aqueous or oleaginous suspensions, may be formulated according to the known art using suitable dispersing or wetting agents and suspending agents.

Preferably, the compositions of the invention are administered via oral route.

Solid dosage forms for oral administration may include capsules, tablets, pills, powders, and granules. In such solid dosage forms, the compound is ordinarily combined with one or more adjuvants appropriate to the indicated route of administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

In order to selectively control the release of the active compound to a particular region of the gastrointestinal tract, the pharmaceutical compositions of the invention may be manufactured into one or several dosage forms for the controlled, sustained or timed release of one or more of the ingredients, as known in the art.

The amount of the compound of the invention that may be combined with the excipient materials to produce a single dosage of the composition will vary depending upon the subject and the particular mode of administration, as known in the art.

The pharmaceutical composition of the invention may further comprise another one or more therapeutic compounds. Therefore, another aspect of the present invention encompasses a combination of a compound of formula (I) as described above, with one or more therapeutic compounds. The therapeutic compound is preferably selected from antibiotics, anticancer agents, steroidal and non-steroidal anti-inflammatory drugs, advantageously it is an anticancer agent.

The antibiotic is preferably selected from the group consisting of beta-lactams, aminoglycosides, tetracyclines, glycylcyclines, macrolides, azalides, ketolides, synergistins, lincosanides, fluoroquinolones, phenicols, rifamycins, sulfamides, trimethoprim, glycopeptides, oxazolidinones, nitromidazoles and lipopeptides.

The non-steroidal anti-inflammatory drug is preferably selected from the group consisting of salicylate and salts thereof, Celecoxib, Diclofenac and salts thereof, Diflunisal, Etodolac, Fenoprofen, Flurbiprofen, Ibuprofen, Indomethacin, Ketoprofen, Meclofenamate, Mefenamic acid, Meloxicam, Nabumetone, Naproxen, Oxaprozin, Piroxicam, Rofecoxib Salsalate, Sulindac, Tolmetin, and Valdecoxib.

The steroidal anti-inflammatory drug is preferably selected from the group consisting of Prednisone, Methylprednisolone, Prednisolone, aldosterone, cortisol, cortisone, hydrocortisone, corticosterone, tixocortol, ciclesonide, prednicarbate Triamcinolone acetonide, triamcinolone alcohol, mometasone, amcinonide, budesonide, desonide, fluocinonide, fluocinolone acetonide, halcinonide, Hydrocortisone-17-valerate, halometasone, alclometasone, betamethasone, prednicarbate, clobetasone-17-butyrate, clobetasol-17-propionate, fluocortolone, fluocortolone, fluprednidene acetate, dexamethasone, and mixtures thereof, and the corresponding salts or hydrates thereof.

The anticancer agent is preferably cisplatine, methotrexate, cyclophosphamide, doxorubicin, fluorouracil.

In some embodiments, the combination comprises 1, 2, 3, 4, or 5 therapeutic compounds, preferably one therapeutic compound.

In another aspect, the present invention relates to a kit comprising at least:
  a first composition comprising the compound of formula (I) as defined above or below, and a pharmaceutically acceptable excipient, and
  a second composition comprising another therapeutic agent, preferably selected from antibiotics, anticancer agents, steroidal and non-steroidal anti-inflammatory drugs, advantageously an anticancer agent,
as a combination product for simultaneous, staggered or sequential use. The kit of the invention is used as drug, in particular for treating an EBV-related cancer.

The antibiotics, anticancer agent, steroidal and non-steroidal anti-inflammatory drug is in particular as listed above in connection with the pharmaceutical composition for use of the invention.

Therapeutic Use

The compound or the composition or the kit of the invention is useful as a drug, typically for disrupting the GAr-based EBNA1 immune evasion of EBV, in particular by preventing the limitation of EBNA1 production in EBV-infected cells.

Consequently, the compound or the composition or the kit of the invention is in particular useful for stimulating the immune response towards EBNA1, and/or EBV-infected cells.

As a result, the compound or the composition or the kit of the invention is in particular useful for preventing and/or treating an EBV-related cancer.

The mechanism of action of the compound or the composition or the kit of the invention in preventing and/or treating an EBV-related cancer is advantageously related to their binding to G4 structures formed by mRNA and EBNA1. Such a mechanism is demonstrated by the results of in vitro experiments showing the binding of the compounds of the present invention to G4-EBNA1 structures. Contrary to the prior art, the anti-cancer action is not related to complexation of a metal cation such as iron.

As used herein, an EBV-related cancer□ is understood as a cancer which is linked to the oncogenic Epstein-Barr virus. In particular, an □EBV-related cancer□ is understood as a cancer wherein more than 50%, typically more than 90%, in particular more than 95% of tumoral cells are infected by EBV, whereas most non tumoral cells are advantageously not infected by EBV. Typically, only some B-cells (memory cells) are also infected by EBV in an EBV-related cancer.

Such a profile of infection by EBV explains the specificity of the compounds of the invention in a method for treating EBV-related cancers.

Detection of EBV in cancers is routine for the pathologists and is based mainly on three main techniques detailed hereafter. The most sensitive technique is in situ hybridization of EBV-encoded RNAs, so-called EBERS (Weiss, L. M. et al, 1989, *Am J Surg Pathol*, 13, 625-631; Chang K. L. et al, 1992, *Diagn Mol Pathol*, 1, 246-255). The presence of EBNA1 and other EBV-related antigens is also commonly used for immunohistochemistry (Grsssser, F A et al., 1994, *Blood*, 84, 3792-3798). These two techniques can be used on frozen or paraffin embedded material. It is also possible to lyse the tumour samples and detect EBV DNA using Polymerase Chain Reaction (Akao et al., 1991, *Laryngoscope*, 101, 279-283).

Therefore, in a particular embodiment, the compound or the composition or the kit of the invention is used in combination, simultaneously, separately or sequentially, with ionizing or non-ionizing radiations or hyperthermia.

In particular, said EBV-related cancer is: Hodgkin's lymphoma, Burkitt's lymphoma, Nasopharyngeal carcinoma, some gastric cancers (about 10% are related to EBV infection), lymphomas in immunosuppressed patients (such as AIDS-suffering patients, post-transplant patients), T/NK cell lymphomas (such as nasal T/NK lymphoma, aggressive NK-cell leukaemia, T cell lymphoproliferative disorder of childhood).

The □effective dose□ of a compound of the invention varies as a function of numerous parameters such as, for example, the route of administration and the weight, the age, the sex, the advancement of the pathology to be treated and the sensitivity of patient to be treated.

As used herein, "patient" includes any mammal, and is preferably a human being.

Definitions

The term ☐halogen☐, as used in the present invention, refers to a fluorine, bromine, chlorine or iodine atom, preferably a chlorine, bromine or fluorine atom.

The term ☐$C_1$-$C_6$)alkyl☐, as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl.

The term ☐($C_1$-$C_6$)haloalkyl☐, as used in the present invention, refers to a straight or branched saturated hydrocarbon chain containing from 1 to 6 carbon atoms substituted with halogen atoms, such as chlorine, bromine, iodine or fluorine atoms, preferably chlorine or fluorine atoms. Examples of ($C_1$-$C_6$)haloalkyl include, but are not limited to, $CH_2Cl$, $CH_2Br$, $CH_2I$, $CH_2F$, $CHF_2$, $CF_3$, $CH_2CH_2Cl$, $CH_2CH_2BR$, $CH_2CH_2$, $CH_2CH_2F$.

The term ☐($C_2$-$C_6$)alkenyl☐, as used in the present invention, refers to a straight or branched unsaturated hydrocarbon chain containing from 2 to 6 carbon atoms and comprising at least one double bond including, but not limited to, ethenyl, propenyl, butenyl, pentenyl, hexenyl.

The term ☐($C_3$-$C_8$)cycloalkyl☐, as used in the present invention, refers to a hydrocarbon monocyclic or bicyclic (fused) ring having 3 to 8 carbon atoms including, but not limited to, cyclopropyl, cyclopentyl, cyclohexyl.

The term ☐($C_5$-$C_{10}$)cycloalkenyl☐, as used in the present invention, refers to a hydrocarbon monocyclic or bicyclic (fused) ring having 5 to 10 carbon atoms and comprising at least one double bond including, but not limited to, cyclopentenyl, cyclohexenyl.

The term ☐heterocycloalkyl☐, as used in the present invention, refers to a hydrocarbon monocyclic or bicyclic (fused) ring having 3 to 8 ring atoms, containing at least one heteroatom, preferably 1 or 2 heteratoms, in the ring. The heteroatom is preferably selected from O, N or S, and the S atom may be mono or dioxidized, i.e. the sulphur atom may be S, S(O) or $SO_2$. heterocycloalkyls include, but are not limited to, epoxide, aziridine, pyrrolidinyl, tetrahydrofuranyl, tetrahydrothiophenyl, tetrahydropyranyl, piperidinyl, piperazinyl, morpholinyl, thiomorpholinyl.

The term ☐heterocycloalkenyl☐, as used in the present invention, refers to a hydrocarbon monocyclic or bicyclic (fused) ring having 5 to 8 ring atoms, containing at least one heteroatom, preferably 1 or 2 heteratoms, in the ring, and comprising at least one double bond. The heteroatom is preferably selected from O, N or S, and the S atom may be mono or dioxidized, i.e. the sulphur atom may be S, S(O) or $SO_2$. heterocycloalkenyls include, but are not limited to, pyrrolyl, dihydrofuranyl, dihydrothiophenyl, dihydropyranyl, tetrahydropyridinyl, dihydrooxazinyl, oxindolyl, benzothiazinyl, benzothiazinonyl, phthalimidyl, indolinyle, isoindolinyle.

As used herein, an ☐aryl group☐ may be an aromatic or heteroaromatic group.

The term "aromatic group" as used herein alone or as part of another group denotes optionally substituted homocyclic aromatic groups, preferably monocyclic or bicyclic (fused) groups, containing from 6 to 10 carbons in the ring portion, such as phenyl, naphthyl and indenyle. Phenyl and naphthyl are the most preferred aromatic groups.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 to 3 heteroatoms preferably selected from O, N and S in the ring, and may be bonded to the remainder of the molecule through a carbon or heteroatom. Exemplary heteroaromatics include furyl, thiophenyl, pyrrolyl, isoxazolyl, oxazolyl, isothiazolyl, thiazolyl, imidazolyl, triazolyl, pyridyl, pyrimidinyl, pyrazinyl, pyridazinyl, indolyl, isoxindolyl, benzoxazolyl, benzothiazolyl, benzotriazolyl, quinolinyl, isoquinolinyl or naphthyridinyl. Preferably, the heteroaromatic group is selected from a pyridinyl, a pyrimidinyl, quinolinyl, isoquinolinyl, naphthyridinyl. Most preferably, the heteroaromatic group is a pyridine.

As used herein, the term ☐alkylaryl☐ refers to a ($C_1$-$C_6$) alkyl-aryl group. Preferably, the alkylaryl group is a ($C_1$-$C_6$)alkyl-aromatic group such as a benzyl group.

As used herein, an ☐alcohol☐ is understood as a linear or ramified hydrocarbon compound comprising between 1 and 6 carbon atom, substituted with 1 to 3 OH groups. Preferably, an alcohol is a linear or ramified $C_1$-$C_6$ hydrocarbon compound substituted with 1 OH group, such as methanol, ethanol, n-propanol, isopropanol or n-butanol.

The term ☐leaving group☐ as used herein refers to a chemical group which can be easily replaced with a nucleophile during a nucleophilic substitution reaction, the nucleophile being in particular a nitrogen containing heteroaromatic group, such as a pyridinyl or a quinolinyl. Such a leaving group can be in particular a halogen atom or a sulfonate. The sulfonate is in particular a group ☐$OSO_2$— $R_{10}$ with $R_{10}$ representing a ($C_1$-$C_6$)alkyl, aryl, aryl-($C_1$-$C_6$)-alkyl or ($C_1$-$C_6$)-alkyl-aryl group. The sulfonate may be a mesylate ($CH_3$—S($O_2$)O—), a triflate (CF3-S(O)$_2$O—) or a tosylate (p-Me-$C_6H_4$—S(O)$_2$O—). Preferably, the leaving group is an halogen atom or a mesylate group, more specifically an iodine atom, a bromine atom or a mesylate group.

Also, in the present invention, Me stands for methyl and Ph stands for phenyl. More generally, the abbreviations used to refer to chemical groups have the meaning commonly known in the art.

DESCRIPTION OF THE FIGURES

FIG. 5 shows a western blot identifying the presence of different proteins (OVA and 235GAr-OVA relatively to GAPDH) in H1299 cells after treatment with compound 2a.

Figure 1:
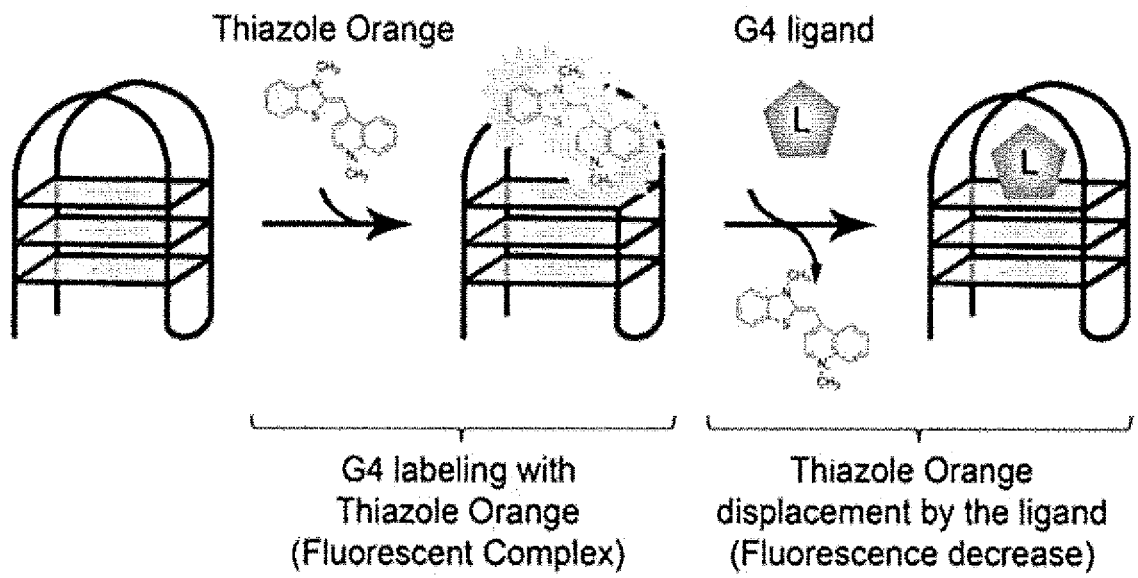
FIG. 1 shows a scheme representing the principles of a G4-FID assay.

Of note, DMSO is an abbreviation for dimethylsulfoxyde.

EXAMPLES

I. Synthesis of Compounds of the Invention

I.1 Synthesis of bis(acylhydrazides)

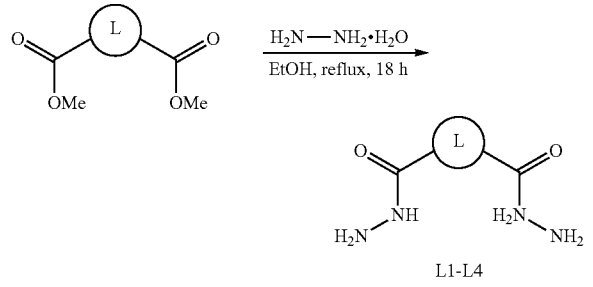

Pyridine-2,6-dicarbohydrazide (L1): A solution of the dimethyl pyridine-2,6-dicarboxylate (10 mmol, 1.95 g) and hydrazine hydrate (220 mmol, 11.2 g, 10.9 mL) in ethanol (150 mL) was heated in the oil bath under reflux for 18 h and then cooled to room temperature. The precipitate was filtered, twice washed with ethanol, once with ether, and dried. White solid, yield 1.73 g (89%); $^1$H NMR (300 MHz, DMSO-$d_6$): δ=10.63 (s, 2H), 8.13 (s, 3H), 4.63 (s, 4H). MS (ESI$^+$): m/z=196.2 [M+H]$^+$.

Pyrimidine-4,6-dicarbohydrazide (L2) was obtained by the same experimental procedure from 4,6-dimethyl pyrimidine-4,6-dicarboxylate. Yield 1.81 g (92%). Pale-yellow solid; $^1$H NMR (300 MHz, DMSO-$d_6$): δ=10.41 (s, 2H), 9.35 (d, J=1.1 Hz, 1H), 8.35 (d, J=1.1 Hz, 1H), 4.77 (s, 4H); MS (ESI$^+$): m/z=197.1 [M+H]$^+$.

1,8-Naphthyridine-2,7-dicarbohydrazide (L3) was obtained by the same experimental procedure from 2,7-dimethyl-1,8-naphthyridine-2,7-dicarboxylate (which is obtained as described by G. Newkome et al., *J Org Chem* 1990, 55, 2838–2842). Yield 2.45 g (97%). Pale-yellow solid; $^1$H NMR (300 MHz, DMSO-$d_6$): δ=10.00 (s, 2H), 8.74 (d, J=8.4 Hz, 2H), 8.25 (d, J=8.4 Hz, 2H), 4.74 (s, 4H); MS (ESI$^+$): m/z=247.1 [M+H]$^+$.

1,10-Phenanthroline-2,9-dicarbohydrazide (L4) was obtained by the same experimental procedure from 2,9-dimethyl-1,10-phenanthroline-2,9-dicarboxylate (which is obtained as described by C. Chandler et al., *J Heterocycl Chem* 1981, 18, 599–601). Yield 2.38 g (80%). Pale yellow solid; $^1$H NMR (300 MHz, DMSO-$d_6$): δ=10.77 (s, 2H), 8.69 (d, J=8.3 Hz, 2H), 8.40 (d, J=8.3 Hz, 2H), 8.14 (s, 2H), 4.78 (s, 4H). MS (ESI$^+$): m/z=297.2 [M+H]$^+$.

I.2 Synthesis of bis(acylhydrazone) Precursors (Compounds 1, 2, 3, 4, 5, 6, 7, 8, 9, 10, 11, and 12)

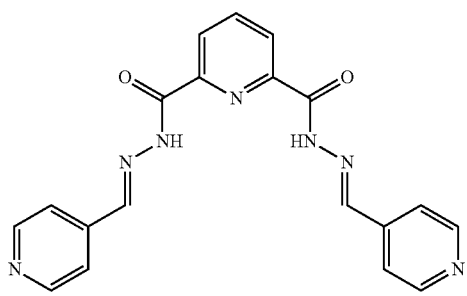 [SMILES: O=C(N/N=C/c1ccncc1)c1cccc(C(=O)N/N=C/c2ccncc2)n1]

N'$^2$,N'$^6$-Bis(pyridin-4-ylmethylene)pyridine-2,6-dicarbohydrazide (1): A solution of pyridine-2,6-dicarbohydrazide L1 (390 mg, 2.0 mmol) and pyridine-4-carbaldehyde (471 mg, 4.4 mmol, 0.414 mL) in ethanol (10 mL) was heated under reflux for 18 h. After cooling, the precipitate was collected by filtration, washed with ethanol, and dried, to give compound 1 (672 mg, 90%) as a white powder. $^1$H NMR (300 MHz, DMSO-$d_6$): δ=12.54 (s, 2H), 8.79 (s, 2H), 8.72 (d, J=5.9 Hz, 4H), 8.44–8.25 (m, 3H), 7.77 (d, J=6.0 Hz, 4H); MS (ESI$^+$): m/z=374.2 [M+H]$^+$, 187.6 [M+2H]$^{2+}$.

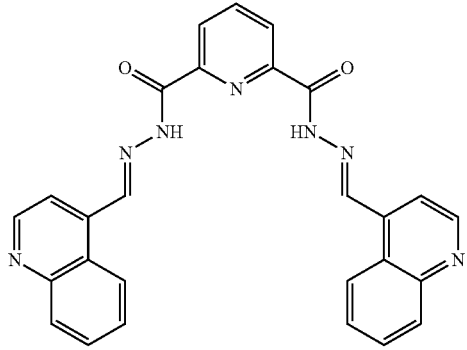 [SMILES: O=C(N/N=C/c1ccnc2ccccc12)c1cccc(C(=O)N/N=C/c2ccnc3ccccc23)n1]

N'$^2$,N'$^6$-Bis(quinolin-4-ylmethylene)pyridine-2,6-dicarbohydrazide (2): Was obtained by following the same experimental procedure in 93% yield from pyridine-2,6-dicarbohydrazide L1 and quinoline-4-carbaldehyde. Pale-yellow solid; $^1$H RMN (300 MHz, DMSO-$d_6$): δ=12.65 (s, 2H), 9.48 (s, 2H), 9.07 (d, J=4.5 Hz, 2H), 8.91 (dd, J=8.4, 0.7 Hz, 2H), 8.53–18.33 (m, 3H), 8.16 (dd, J=8.3, 0.7 Hz, 2H), 7.99 (d, J=4.5 Hz, 2H), 7.92–7.79 (m, 4H); MS (ESI$^+$): m/z=474.3 [M+H]$^+$.

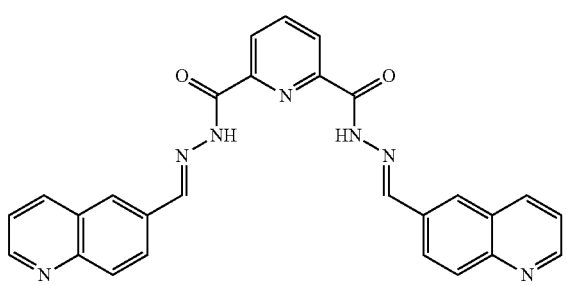 [SMILES: O=C(N/N=C/c1ccc2ncccc2c1)c1cccc(C(=O)N/N=C/c2ccc3ncccc3c2)n1]

N'². N'⁶-Bis(quinolin-6-ylmethylene)pyridine-2,6-dicarbohydrazide (3): Was obtained by following the same experimental procedure in 80% yield from pyridine-2,6-dicarbohydrazide L1 and quinoline-6-carbaldehyde. Pale-yellow solid; ¹H NMR (300 MHz, DMSO-d₆): δ=12.50 (s, 2H), 9.01-8.94 (m, 4H), 8.52 (d, J=7.8 Hz, 2H), 8.46☐8.39 (m, 2H), 8.39☐8.28 (m, 5H), 8.13 (d, J=8.8 Hz, 2H), 7.63 (dd, J=8.3, 4.3 Hz, 2H); MS (ESI⁺): m/z=474.3 [M+H]⁺, 237.7 [M+2H]²⁺.

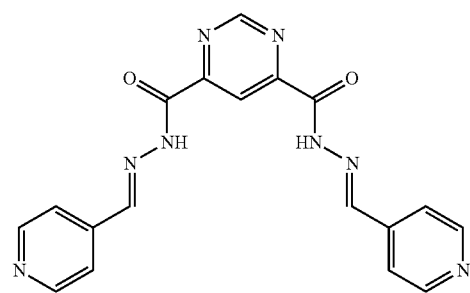 [SMILES: O=C(N/N=C/c1ccncc1)c1cc(C(=O)N/N=C/c2ccncc2)ncn1]

N'⁴,N'⁶-Bis(pyridin-4-ylmethylene)pyrimidine-4,6-dicarbohydrazide (4): Was obtained by following the same experimental procedure in 99% yield from pyrimidine-4,6-dicarbohydrazide L2 and pyridine-4-carbaldehyde. White solid; ¹H NMR (300 MHz, DMSO-d₆): δ=12.79 (s, 2H), 9.59 (d, J=0.8 Hz, 1H), 8.71 (s, 2H), 8.69 (d, J=5.8 Hz, 4H), 8.61 (d, J=0.8 Hz, 1H), 7.70 (d, J=5.8 Hz, 4H); MS (ESI⁺): m/z=375.2 [M+H]⁺, 188.1 [M+2H]²⁺.

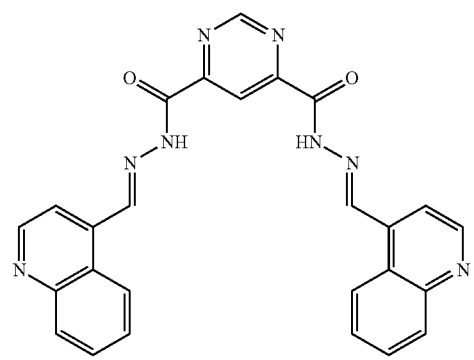 [SMILES: O=C(N/N=C/c1ccnc2ccccc12)c1cc(C(=O)N/N=C/c2ccnc3ccccc23)ncn1]

N'⁴,N'⁶-Bis(quinolin-4-ylmethylene)pyrimidine-4,6-dicarbohydrazide (5): Was obtained by following the same experimental procedure in 99% yield from pyrimidine-4,6-dicarbohydrazide L2 and quinoline-4-carbaldehyde. Pale-yellow solid; ¹H NMR (300 MHz, DMSO-d₆): δ=12.86 (s, 2H), 9.67 (s, 1H), 9.48 (s, 2H), 9.04 (d, J=4.3 Hz, 2H), 8.80☐8.65 (m, 3H), 8.14 (d, J=8.3 Hz, 2H), 7.95☐7.72 (m, 6H); MS (ESI⁺): m/z=475.3 [M+H]⁺, 238.2 [M+2H]²⁺.

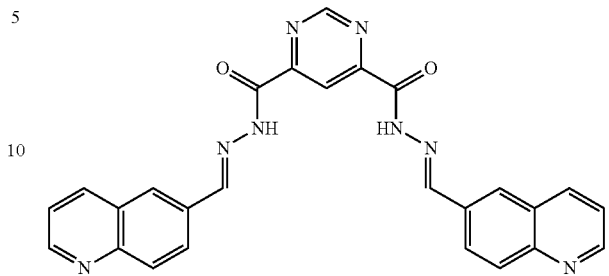

N'⁴,N'⁶-Bis(quinolin-6-ylmethylene)pyrimidine-4,6-dicarbohydrazide (6): Was obtained by following the same experimental procedure in 99% yield from pyrimidine-4,6-dicarbohydrazide L2 and quinoline-6-carbaldehyde. Pale-yellow solid; ¹H NMR (300 MHz, DMSO-d₆): δ=12.68 (s, 2H), 9.60 (s, 1H), 9.03-8.87 (m, 4H), 8.65 (s, 1H), 8.51 (d, J=8.0 Hz, 2H), 8.32☐8.20 (m, 4H), 8.10 (d, J=8.4 Hz, 2H), 7.66☐7.55 (m, 2H); MS (ESI⁺): m/z=475.3 [M+H]⁺, 238.2 [M+2H]²⁺.

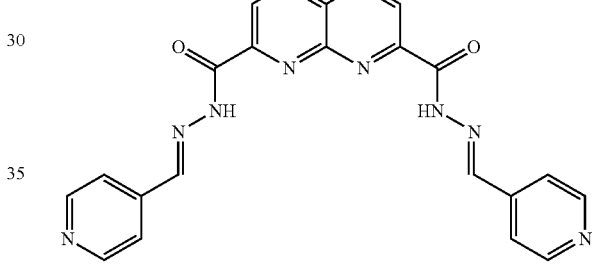

N'²,N'⁷-Bis(pyridin-4-ylmethylene)-1,8-naphthyridine-2,7-dicarbohydrazide (7): Was obtained by following the same experimental procedure in 78% yield from 1,8-naphthyridine-2,7-dicarbohydrazide L3 and pyridine-4-carbaldehyde. White solid; ¹H NMR (300 MHz, DMSO-d₆): δ 12.63 (s, 2H), 8.89 (d, J=8.3 Hz, 2H), 8.81☐8.58 (m, 6H), 8.42 (d, J=8.3 Hz, 2H), 7.71 (d, J=4.6 Hz, 4H); MS (ESI⁺): m/z=425.1 [M+H]⁺.

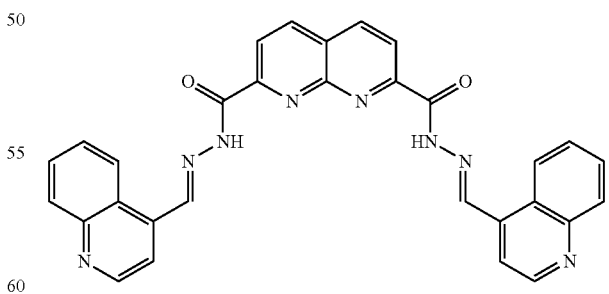

N'²,N'⁷-Bis(pyridin-4-ylmethylene)-1,8-naphthyridine-2,7-dicarbohydrazide (8): Was obtained by following the same experimental procedure in 80% yield from 1,8-naphthyridine-2,7-dicarbohydrazide L3 and quinoline-4-carbaldehyde. White solid; ¹H NMR (300 MHz, DMSO-d₆): δ=12.72 (s, 2H), 9.51 (s, 2H), 9.05 (d, J=4.5 Hz, 2H), 8.93 (d, J=8.3

Hz, 2H), 8.78 (d, J=8.3 Hz, 2H), 8.48 (d, J=8.3 Hz, 2H), 8.14 (d, J=8.2 Hz, 2H), 7.95 (d, J=4.4 Hz, 2H), 7.90☐7.84 (m, 2H), 7.84☐7.77 (m, 2H); MS (ESI⁺): m/z=525.2 [M+H]⁺, 263.2 [M+2H]²⁺.

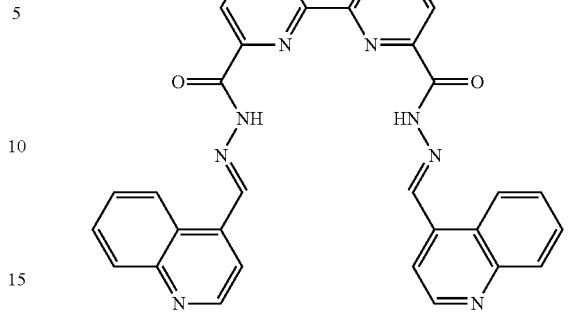

$N^{'2}$,$N^{'9}$-Bis(quinolin-4-ylmethylene)-1,10-phenanthroline-2,9-dicarbohydrazide (11): Was obtained by following the same experimental procedure in 55% yield from 1,10-phenanthroline-2,9-dicarbohydrazide L4 and quinoline-4-carbaldehyde. ¹H NMR (300 MHz, DMSO-d₆): δ=12.97 (s, 2H), 9.62 (s, 2H), 8.86-8.83 (m, 4H), 8.65 (d, J=8.3 Hz, 2H), 8.61 (d, J=8.2 Hz, 2H), 8.26 (s, 2H), 7.99 (d, J=8.3 Hz, 2H), 7.81 (d, J=4.5 Hz, 2H), 7.61☐7.53 (m, 2H), 7.10☐7.02 (m, 2H); MS (ESI⁺): m/z=575.3 [M+H]⁺ 288.2 [M+2H]²⁺.

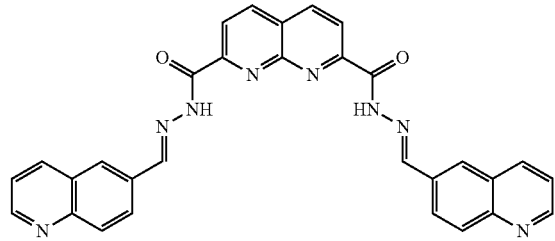 [SMILES: O=C(N/N=C/c1ccc2ncccc2c1)c1ccc2ccc(C(=O)N/N=C/c3ccc4ncccc4c3)nc2n1]

$N^{'2}$,$N^{'7}$-Bis(pyridin-6-ylmethylene)-1,8-naphthyridine-2,7-dicarbohydrazide (9): Was obtained by following the same experimental procedure in 80% yield from 1,8-naphthyridine-2,7-dicarbohydrazide L3 and quinoline-6-carbaldehyde. White solid; ¹H NMR (300 MHz, DMSO-d₆): δ=12.56 (s, 2H), 9.07-8.74 (m, 6H), 8.52 (d, J=8.3 Hz, 2H), 8.44 (d, J=8.2 Hz, 2H), 8.33☐8.25 (m, 4H), 8.12 (d, J=8.9 Hz, 2H), 7.62 (dd, J=7.6, 4.0 Hz, 2H); MS (ESI⁺): m/z=263.1 [M+2H]²⁺.

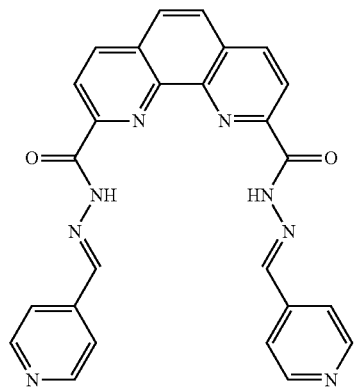 [SMILES: O=C(N/N=C/c1ccncc1)c1ccc2ccc3ccc(C(=O)N/N=C/c4ccncc4)nc3c2n1]

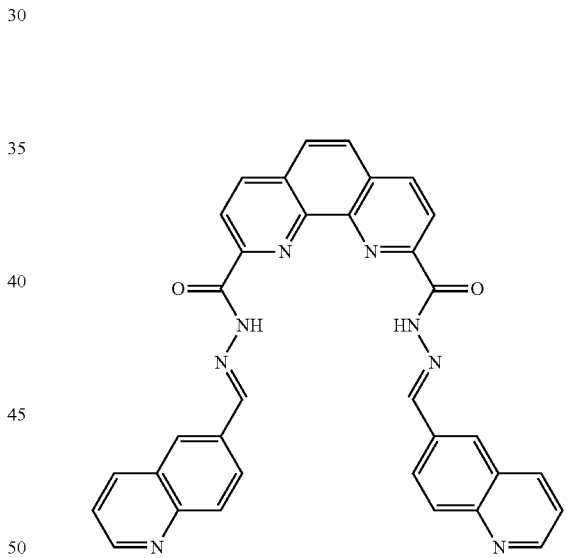

$N^{'2}$,$N^{'9}$-Bis(pyridin-4-ylmethylene)-1,10-phenanthroline-2,9-dicarbohydrazide (10): Was obtained by following the same experimental procedure in 77% yield from 1,10-phenanthroline-2,9-dicarbohydrazide L4 and pyridine-4-carbaldehyde. Pale yellow solid; ¹H NMR (300 MHz, DMSO-d₆): δ=12.96 (s, 2H), 8.92 (s, 2H), 8.85 (d, J=8.3 Hz, 2H), 8.77 (d, J=1.3 Hz, 2H), 8.75 (d, J=1.3 Hz, 2H), 8.61 (d, J=8.3 Hz, 2H), 8.28 (s, 2H), 7.75 (d, J=1.3 Hz, 2H), 7.73 (d, J=1.3 Hz, 2H); MS (ESI⁺): m/z=475.3 [M+H]⁺.

$N^{'2}$,$N^{'9}$-Bis(quinolin-6-ylmethylene)-1,10-phenanthroline-2,9-dicarbohydrazide (12): Was obtained by following the same experimental procedure in 59% yield from 1,10-phenanthroline-2,9-dicarbohydrazide and quinoline-6-carbaldehyde. ¹H NMR (300 MHz, DMSO-d₆): δ=12.94 (s, 2H), 9.17 (s, 2H), 8.96 (d, J=2.8 Hz, 2H), 8.85 (d, J=8.3 Hz, 2H), 8.61 (d, J=8.3 Hz, 2H), 8.35 (d, J=8.8 Hz, 2H), 8.28 (s, 2H), 8.23 (s, 2H), 8.13 (d, J=8.8 Hz, 2H), 8.08 (d, J=8.0 Hz, 2H), 7.51 (dd, J=8.2, 4.2 Hz, 2H); MS (ESI⁺): m/z=575.3 [M+H]⁺, 288.2 [M+2H]²⁺.

I.3 Synthesis of Quaternized bis(acylhydrazone)s
General Procedure A:

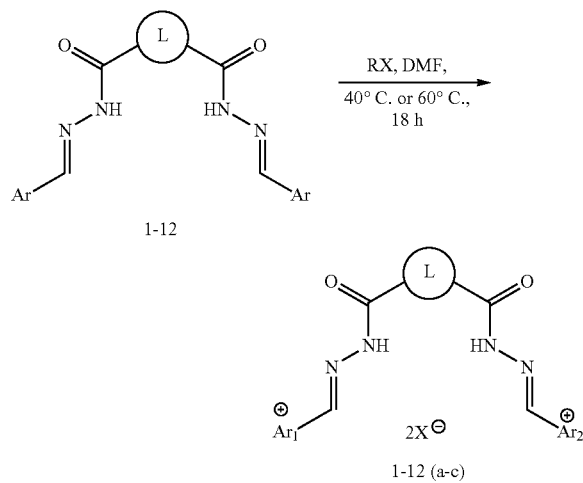

R = methyl, ethyl or benzyl

A mixture of compound 1-12 (0.5 mmol), RX (iodomethane (75 mmol), iodoethane (75 mmol) or benzyl bromide (10 mmol)) and DMF (3 mL) was sealed in a tube and heated at 40° C. or 60° C. during 18 h. After cooling to room temperature, the precipitate was filtered and washed with DMF and diethyl ether. Finally, the product was dried in vacuum and purified by recrystallization from boiling MeCN/H$_2$O to afford the desired compounds 1-12 (a-c).

General Procedure B:

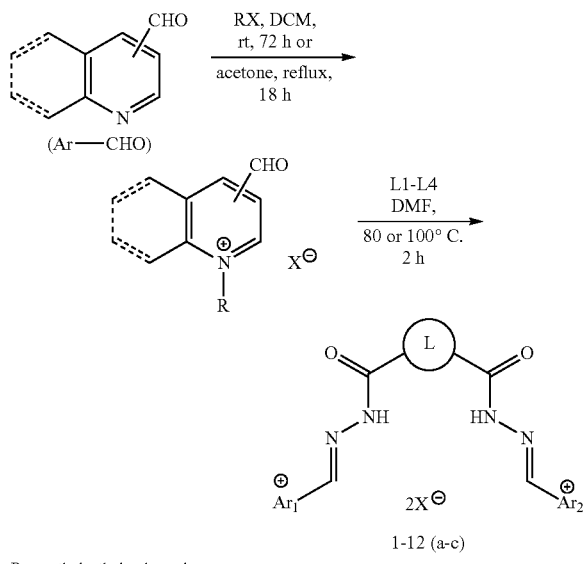

R = methyl, ethyl or benzyl

A solution of the aldehyde (Ar—CHO, 10 mmol) and the alkylating agent RX (100 mmol) in acetone (18 mL) was stirred at 60° C. for 18 h then cooled to room temperature. The precipitated solid was filtered, washed twice with acetone, once with ether, and dried. The resulting quaternized aldehyde (1.1 mmol) was mixed with bis(acylhydrazide) L1-L4 (0.5 mmol) in DMF (3 mL) and the resulting mixture was heated at 100° C. (80° C. for 9c and 12c) for 2 h and then cooled to room temperature. The precipitate was collected by filtration, washed three times with MeCN, once with ether, dried and then additionally recrystallized from MeCN/H$_2$O.

$N'^2,N'^6$-Bis[(1-methylpyridinium-4-yl)methylene]pyridine-2,6-dicarbohydrazide iodide (1a): Was obtained from compound 1 (186.7 mg, 0.5 mmol), iodomethane (9.3 mL, 10.6 g, 75 mmol) and DMF (3 mL) in 85% yield by following general procedure A. Orange powder. $^1$H NMR (300 MHz, DMSO-d$_6$): δ=12.93 (s, 2H), 9.03 (d, J=5.9 Hz, 4H), 8.94 (s, 2H), 8.54☐8.31 (m, 7H), 4.37 (s, 6H); Hereafter, in the assignment of mass spectra, M refers to the organic dication. MS (ESI$^+$): m/z=530.2 [M+I]$^+$, 201.7 [M]$^{2+}$.

$N'^2$, $N'^6$-Bis[(1-methylquinolinium-4-yl)methylene]pyridine-2,6-dicarbohydrazide iodide (2a): Was obtained from compound 2 (236.7 mg, 0.5 mmol) and iodomethane (9.3 mL, 10.6 g, 75 mmol) in 53% yield by following the general procedure A. Orange solid; $^1$H NMR (300 MHz, DMSO-d$_6$): δ=13.03 (s, 2H), 9.74 (s, 2H), 9.54 (d, J=6.3 Hz, 2H), 9.07 (d, J=8.5 Hz, 2H), 8.66☐8.56 (m, 4H), 8.52 (d, J=7.0 Hz, 2H), 8.48☐8.43 (m, 1H), 8.42☐8.33 (m, 2H), 8.27☐8.18 (m, 2H), 4.68 (s, 6H); MS (ESI$^+$): m/z=502.3 [M☐H]$^+$, 251.8 [M]$^{2+}$.

$N'^2,N'^6$-Bis[(1-benzylquinolinium-4-yl)methylene]pyridine-2,6-dicarbohydrazide bromide (2c): A mixture of compound 2 (236.7 mg, 0.5 mmol), benzyl bromide (1.2 mL, 1.71 g, 10 mmol) and DMF (3 mL) was heated at 60° C. during 18 h. After cooling to room temperature, the precipitate was filtered off and washed with DMF and ether. Finally, the product was dried in vacuum to afford compound 2c (354.8 mg, 87%) in a sufficiently pure form (as assessed by $^1$H NMR and LC/MS), as a yellow-orange powder. $^1$H NMR (300 MHz, DMSO-d$_6$): δ=13.34 (s, 2H), 10.29 (s, 2H), 9.74 (d, J=6.2 Hz, 2H), 9.06 (d, J=8.5 Hz, 2H), 8.66 (d, J=6.2 Hz, 2H), 8.62☐8.50 (m, 4H), 8.49☐8.38 (m, 1H), 8.31☐8.23 (m, 2H), 8.19☐8.11 (m, 2H), 7.41 (s, 10H), 6.42 (s, 4H); MS (ESI$^+$): m/z=654.4 [M☐H]$^+$, 327.8 [M]$^{2+}$.

$N'^2,N'^6$-Bis[(1-ethylquinolinium-6-yl)methylene]pyridine-2,6-dicarbohydrazide iodide (3b): Was obtained from compound 3 (236.7 mg, 0.5 mmol) and iodoethane 6.0 mL, 11.7 g, 75 mmol) in 92% yield by following the same experimental procedure as described for compound 1a. Pale brown solid; $^1$H NMR (300 MHz, DMSO-d$_6$): δ=12.67 (s, 2H), 9.59 (d, J=5.4 Hz, 2H), 9.38 (d, J=8.3 Hz, 2H), 9.07 (s, 2H), 8.85 (s, 2H), 8.74 (q, J=9.6 Hz, 4H), 8.45 (d, J=7.1 Hz, 2H), 8.41☐8.32 (m, 1H), 8.32☐8.16 (m, 2H), 5.14 (q, J=7.0 Hz, 4H), 1.66 (t, J=7.0 Hz, 6H); MS (ESI$^+$): m/z=644.3 [M☐H]$^+$, 265.8 [M]$^{2+}$.

$N'^2,N'^6$-Bis[(1-benzylquinolinium-6-yl)methylene]pyridine-2,6-dicarbohydrazide bromide (3c): Was obtained from compound 3 (236.7 mg, 0.5 mmol) and benzyl bromide (1.2 mL, 1.71 g, 10 mmol) in 65% yield by following the same experimental procedure as described for compound 2c. Pale yellow solid; $^1$H NMR (300 MHz, DMSO-d$_6$): δ=12.72 (s, 2H), 9.76 (d, J=5.0 Hz, 2H), 9.48 (d, J=8.3 Hz, 2H), 9.12 (s, 2H), 8.85 (s, 2H), 8.73☐8.58 (m, 4H), 8.46☐8.30 (m, 5H), 7.49☐7.34 (m, 10H), 6.41 (s, 4H); MS (ESI$^+$): m/z=768.3 [M☐H]$^+$, 327.8 [M]$^{2+}$.

$N'^4,N'^6$-Bis[(1-methylpyridinium-4-yl)methylene]pyrimidine-4,6-dicarbohydrazide iodide (4a): Was obtained from compound 4 (187.2 mg, 0.5 mmol) and iodomethane (9.3 mL, 10.6 g, 75 mmol) in 85% yield by following the same experimental procedure as described for compound 1a. Yellow-orange solid; $^1$H NMR (300 MHz, DMSO-d$_6$): δ=13.31 (s, 2H), 9.67 (s, 1H), 9.01 (d, J=6.5 Hz, 4H), 8.86

(s, 2H), 8.64 (s, 1H), 8.38 (d, J=6.4 Hz, 4H), 4.35 (s, 6H); MS (ESI⁺): m/z=403.3 [M–H]⁺, 202.2 [M]²⁺.

N⁴,N⁶-Bis[(1-methylquinolinium-4-yl)methylene]pyrimidine-4,6-dicarbohydrazide iodide (5a): Was obtained from compound 5 (237.2 mg, 0.5 mmol) and iodomethane (9.3 mL, 10.6 g, 75 mmol) in 97% yield by following the same experimental procedure as described for compound 1a. Orange solid; ¹H NMR (300 MHz, DMSO-d₆): δ=13.28 (s, 2H), 9.75 (s, 1H), 9.70 (s, 2H), 9.51 (d, J=6.2 Hz, 2H), 8.86 (d, J=8.4 Hz, 2H), 8.73 (s, 1H), 8.60 (d, J=8.7 Hz, 2H), 8.52 (d, J=6.1 Hz, 2H), 8.40–8.32 (m, 2H), 8.25–8.16 (m, 2H), 4.67 (s, 6H); MS (ESI⁺): m/z=503.3 [M–H]⁺, 252.3 [M]²⁺.

N'²,N'⁶-Bis[(1-benzylquinolinium-4-yl)methylene]pyridine-2,6-dicarbohydrazide bromide (5c): Was obtained from compound L2 (0.5 mmol) and 4-formyl-1-benzylquinolinium bromide (1.1 mmol) in 93% yield by following general procedure B. Brown crystals. ¹H NMR (300 MHz, DMSO-d₆): δ 13.31 (s, 2H), 9.74 (d, J=5.3 Hz, 5H), 8.85 (d, J=8.7 Hz, 2H), 8.74 (s, 1H), 8.60 (dd, J=17.3, 7.6 Hz, 4H), 8.33–8.22 (m, 2H), 8.20–8.12 (m, 2H), 7.40 (s, 10H), 6.42 (s, 4H); MS (ESI⁺): m/z (%)=655.5 (12) [M–H]⁺, 328.4 (100) [M]²⁺.

N'²,N'⁶-Bis[(1-ethylquinolinium-6-yl)methylene]pyridine-2,6-dicarbohydrazide iodide (6b). Was obtained from compound L2 (0.5 mmol) and 6-formyl-1-ethylquinolinium iodide (1.1 mmol) in 96% yield by following general procedure B. Orange solid. ¹H NMR (300 MHz, DMSO-d₆): δ 12.93 (s, 2H), 9.65 (s, 1H), 9.57 (d, J=5.7 Hz, 2H), 9.37 (d, J=8.3 Hz, 2H), 9.00 (s, 2H), 8.80–8.61 (m, 7H), 8.25 (dd, J=8.3, 5.9 Hz, 2H), 5.12 (q, J=7.2 Hz, 4H), 1.64 (t, J=7.2 Hz, 6H); MS (ESI⁺): m/z (%)=266.3 (100) [M]²⁺.

N'²,N'⁶-Bis[(1-benzylquinolinium-6-yl)methylene]pyridine-2,6-dicarbohydrazide bromide (6c): Was obtained from compound L2 (0.5 mmol) and 6-formyl-1-benzylquinolinium bromide (1.1 mmol) in 97% yield by following general procedure B. Pale-yellow solid. ¹H NMR (300 MHz, DMSO-d₆): δ 12.91 (s, 2H), 9.74 (d, J=5.4 Hz, 2H), 9.62 (d, J=1.2 Hz, 1H), 9.46 (d, J=8.3 Hz, 2H), 8.96 (s, 2H), 8.80 (s, 2H), 8.67–8.55 (m, 5H), 8.34 (dd, J=8.3, 5.9 Hz, 2H), 7.47–7.37 (m, 10H), 6.39 (s, 4H); MS (ESI⁺): m/z (%)=769.5 (7) [M+CF₃COO]⁺, 328.3 (100) [M]²⁺.

N'²,N'⁷-Bis[(1-methylpyridinium-4-yl)methylene]-1,8-naphthyridine-2,7-dicarbohydrazide iodide (7a): Was obtained from compound 7 (212.2 mg, 0.5 mmol) and iodomethane (9.3 mL, 10.6 g, 75 mmol) in 76% yield by following the same experimental procedure as described for compound 1a. Yellow solid; ¹H NMR (300 MHz, DMSO-d₆): δ=13.14 (s, 2H), 9.01 (d, J=6.0 Hz, 4H), 8.94 (d, J=8.3 Hz, 2H), 8.83 (s, 2H), 8.45 (d, J=8.3 Hz, 2H), 8.39 (d, J=5.9 Hz, 4H), 4.36 (s, 6H); MS (ESI⁺): m/z=453.3 [M–H]⁺, 227.3 [M]²⁺.

N'²,N'⁷-Bis[(1-methylquinolinium-4-yl)methylene]-1,8-naphthyridine-2,7-dicarbohydrazide iodide (8a): Was obtained from compound 8 (262.3 mg, 0.5 mmol) and iodomethane (9.3 mL, 10.6 g, 75 mmol) in 81% yield by following the same experimental procedure as described for compound 1a. Red solid; ¹H NMR (300 MHz, DMSO-d₆): δ=13.14 (s, 2H), 9.72 (s, 2H), 9.52 (d, J=6.2 Hz, 2H), 8.99 (d, J=8.3 Hz, 2H), 8.90 (d, J=8.4 Hz, 2H), 8.68–8.47 (m, 6H), 8.39–8.32 (m, 2H), 8.25–8.15 (m, 2H), 4.67 (s, 6H); MS (ESI⁺): m/z=553.3 [M–H]⁺, 277.2 [M]²⁺.

N'²,N'⁷-Bis[(1-benzylquinolinium-4-yl)methylene]-1,8-naphthyridine-2,7-dicarbohydrazide bromide (8c): Was obtained from compound 8 (262.3 mg, 0.5 mmol) and benzyl bromide (1.2 mL, 1.71 g, 10 mmol) in 63% yield by following the same experimental procedure as described for compound 2c. Yellow solid; 1H NMR (300 MHz, DMSO-d₆): δ=13.19 (s, 2H), 9.77 (s, 4H), 9.00 (d, J=8.3 Hz, 2H), 8.90 (d, J=8.1 Hz, 2H), 8.66 (d, J=6.0 Hz, 2H), 8.56 (dd, J=16.8, 8.7 Hz, 4H), 8.32–8.22 (m, 2H), 8.21–8.12 (m, 2H), 7.41 (s, 10H), 6.44 (s, 4H); MS (ESI⁺): m/z=705.4 [M–H]⁺, 353.4 [M]²⁺.

N'²,N'⁷-Bis[(1-ethylquinolinium-6-yl)methylene]-1,8-naphthyridine-2,7-dicarbohydrazide iodide (9b): Was obtained from compound 9 (262.3 mg, 0.5 mmol) and iodoethane (6.0 mL, 11.7 g, 75 mmol) by the same experimental procedure in 80% yield. Pale brown solid; ¹H NMR (300 MHz, DMSO-d₆): δ=12.79 (s, 2H), 9.58 (d, J=5.9 Hz, 2H), 9.38 (d, J=8.6 Hz, 2H), 8.99 (s, 2H), 8.93 (d, J=8.4 Hz, 2H), 8.72 (dd, J=20.4, 11.1 Hz, 6H), 8.45 (d, J=8.3 Hz, 2H), 8.26 (dd, J=8.3, 5.8 Hz, 2H), 5.13 (q, J=7.2 Hz, 4H), 1.65 (t, J=7.1 Hz, 6H); MS (ESI⁺): m/z=291.3 [M]²⁺.

N'²,N'⁷-Bis[(1-benzylquinolinium-6-yl)methylene]-1,8-naphthyridine-2,7-dicarbohydrazide bromide (9c): Was obtained from compound 9 (262.3 mg, 0.5 mmol) and benzyl bromide (1.2 mL, 1.71 g, 10 mmol) in 66% yield by following the same experimental procedure as described for compound 2c. Pale brown solid; ¹H NMR (300 MHz, DMSO-d₆): δ=12.76 (s, 2H), 9.75 (d, J=5.6 Hz, 2H), 9.48 (d, J=8.3 Hz, 2H), 8.98–8.85 (m, 4H), 8.80 (s, 2H), 8.63 (m, 4H), 8.43 (d, J=8.3 Hz, 2H), 8.35 (dd, J=8.2, 5.9 Hz, 2H), 7.41 (d, J=6.6 Hz, 10H), 6.40 (s, 4H); MS (ESI⁺): m/z=705.4 [M–H]⁺, 353.2 [M]²⁺.

N'²,N'⁹-Bis[(1-methylpyridinium-4-yl)methylene]-1,10-phenanthroline-2,9-dicarbohydrazide iodide (10a): Was obtained from compound 10 (237.2 mg, 0.5 mmol) and iodomethane (9.3 mL, 10.6 g, 75 mmol) in 49% yield by following the same experimental procedure as described for compound 1a. Yellow solid; ¹H NMR (300 MHz, DMSO-d₆): δ=13.38 (s, 2H), 9.04 (s, 6H), 8.89 (d, J=8.1 Hz, 2H), 8.64 (d, J=8.0 Hz, 2H), 8.41 (d, J=5.9 Hz, 4H), 8.32 (s, 2H), 4.41 (s, 6H), MS (ESI⁺): m/z=705.4 [M–H]⁺, 353.4 [M]²⁺.

N'²,N'⁹-Bis[(1-methylquinolinium-4-yl)methylene]-1,10-phenanthroline-2,9-dicarbohydrazide iodide (11a): Was obtained from compound 11 (287.3 mg, 0.5 mmol) and iodomethane (9.3 mL, 10.6 g, 75 mmol) in 85% yield by following the same experimental procedure as described for compound 1a. Dark-red solid; ¹H NMR (300 MHz, DMSO-d₆): δ=13.28 (s, 2H), 9.86 (s, 2H), 9.45 (d, J=6.3 Hz, 2H), 8.95 (d, J=8.3 Hz, 2H), 8.71 (d, J=8.3 Hz, 2H), 8.56 (d, J=6.1 Hz, 2H), 8.48–8.34 (m, 4H), 8.27 (d, J=9.1 Hz, 2H), 7.88–7.80 (m, 2H), 7.15–7.08 (m, 2H), 4.62 (s, 6H); MS (ESI⁺): m/z=717.3 [M+CF₃COO]⁺, 603.4 [M–H]⁺, 302.3 [M]²⁺.

N'²,N'⁹-Bis[(1-benzylquinolinium-4-yl)methylene]-1,10-phenanthroline-2,9-dicarbohydrazide bromide (11c): Was obtained from compound 11 (287.3 mg, 0.5 mmol) and benzyl bromide (1.2 mL, 1.71 g, 10 mmol) in 75% yield by following the same experimental procedure as described for compound 2c. Pale brown solid; ¹H NMR (300 MHz, DMSO-d₆): δ=13.34 (s, 2H), 9.94 (s, 2H), 9.76 (d, J=6.0 Hz, 2H), 8.96 (d, J=8.2 Hz, 2H), 8.73 (d, J=7.7 Hz, 4H), 8.37 (d, J=7.9 Hz, 4H), 8.14 (d, J=9.2 Hz, 2H), 7.65–7.30 (m, 10H), 7.09–7.00 (m, 2H), 6.84–6.79 (m, 2H), 6.35 (s, 4H); MS (ESI⁺): m/z=378.4 [M]²⁺.

N'²,N'⁹-Bis[(1-ethylquinolinium-6-yl)methylene]-1,10-phenanthroline-2,9-dicarbohydrazide iodide (12b): Was obtained from compound 12 (287.3 mg, 0.5 mmol) and iodoethane (6.0 mL, 11.7 g, 75 mmol) in 85% yield by following the same experimental procedure as described for compound 1a. Pale brown solid; ¹H NMR (300 MHz, DMSO-d₆): δ=13.10 (s, 2H), 9.60 (d, J=5.6 Hz, 2H), 9.25 (s, 2H), 9.17 (d, J=8.2 Hz, 2H), 8.89 (d, J=8.3 Hz, 2H), 8.76 (d, J=2.6 Hz, 6H), 8.64 (d, J=8.3 Hz, 2H), 8.32 (s, 2H), 8.22 (dd, J=8.4, 5.9 Hz, 2H), 5.16 (q, J=7.0 Hz, 4H), 1.67 (t, J=7.1 Hz, 6H); MS (ESI+): m/z=705.4 [M☐H]+, 353.4 [M]$^{2+}$.

N$^{t2}$,N$^{t9}$-Bis[(1-benzylquinolinium-6-yl)methylene]-1,10-phenanthroline-2,9-dicarbohydrazide bromide (12c): Was obtained from compound 12 (287.3 mg, 0.5 mmol) and benzyl bromide (1.2 mL, 1.71 g, 10 mmol) in 73% yield by following the same experimental procedure as described for compound 2c. Pale brown solid; $^1$H NMR (300 MHz, DMSO-d$_6$): δ=13.10 (s, 2H), 9.79 (d, J=5.7 Hz, 2H), 9.30 (d, J=8.3 Hz, 2H), 9.21 (s, 2H), 8.87 (d, J=8.3 Hz, 2H), 8.81 (s, 2H), 8.76☐8.65 (m, 4H), 8.63 (d, J=8.3 Hz, 2H), 8.39☐8.28 (m, 4H), 7.53☐7.37 (m, 10H), 6.46 (s, 4H). MS (ESI+): m/z=378.4 [M]$^{2+}$.

II. FID (Fluorescent Indicator Displacement) Assay

1. Principle

This assay is based on the displacement of a fluorescent indicator (Thiazole Orange, hereinafter TO) from a G4-RNA structure (RNA G-quadruplex of EBNA1) by a putative ligand such as the compounds of the invention (see FIG. 1). This displacement is quantified as % TO displacement. The percentage of TO displacement is calculated from the fluorescence intensity (F) in the presence of a putative ligand, using:

$$\% \; TO \; \text{displacement} = 1 - \frac{F}{F_0}$$

where $F_0$ is fluorescence intensity of the probe (TO) bound to RNA without added ligand. The percentage of displacement is then plotted as a function of the concentration of added ligand. The RNA affinity of putative ligands is evaluated using the concentration of a ligand required to decrease the fluorescence of the probe by 50% (noted $DC_{50}$), which is determined graphically from non-linear fitting of the displacement curve. Low $DC_{50}$ values ($DC_{50}$<0.25 μM) typically indicate strong affinity of the ligand to G4-RNA.

2. Materials and Reagents

Thiazole Orange (TO) and cacodylic acid were purchased from Aldrich and used without further purification. The oligoribonucleotide EBNA1 [5'-r(GGGGCAGGAGCAG-GAGGA)-3'] (SEQ ID no 1) purified by reversed-phase HPLC was purchased from Eurogentec.

Stock solutions of the ligands (2 mM in DMSO (dimethylsulfoxyde)) were used for G4-FID assay, unless otherwise stated, and were stored at −20° C. Stock solutions of TO (2 mM in DMSO) were used for G4-FID assay. Fluorescent probe powders and solutions were stored and used, protected from light and used as aliquots to avoid freeze-thaw cycles. HT-G4-FID measurements were performed on a FLUOstar Omega microplate reader (BMG Labtech) with 96-well Non-Binding Surface black with black bottom polystyrene microplates (Corning ref 3650).

3. Spectroscopic Measurements

Preparation of the Oligonucleotide

For HT-G4-FID assay, the oligonucleotide was dissolved in K$^+$-100-buffer (10 mM lithium cacodylate, pH 7.3, 100 mM KCl, 1 mM EDTA, 1% DMSO). Oligonucleotide concentrations were determined on the basis of their absorbance at 260 nm. Prior to use, the oligonucleotide was pre-treated by heating at 95° C. for 5 min followed by a slow cooling to 25° C.

HT-G4-FID Assay

Each G4-FID assay is performed in a 96-well microplates. Every ligand (compound) is tested on a line of the microplate, in duplicate (in other plate). The microplate is filled with (a) K$^+$-100 solution (qs for 200 μL) (b) 10 μL of a solution of pre-folded oligonucleotides (5 μM) and TO (10 μM-2 eq) and (c) an extemporaneously prepared 5 μM ligand solution in K$^+$-100 buffer (0 to 100 μL along the line of the microplate, i.e., from column A to column H: 0, 0.125, 0.25, 0.375, 0.5, 0.625, 0.75, 1.0, 1.25, 1.5, 2.0 and 2.5 μM) (see Largy et al., Anal Bioanal Chem 2011, 400, 34193427). After 5 min of orbital shaking at 500 rpm, fluorescence intensity is measured using the following experimental parameters: positioning delay: 0.5 s, 20 flashes per well, emission/excitation filters (nm): 485/520, gain adjusted at 80% of the fluorescence from the most fluorescent well (i.e., a well from column A).

4. Results

Results are shown in Table 1 below (lower $DC_{50}$ values indicate higher affinity of compounds to the G4-RNA structure of EBNA1). These results are based on triplicate assays.

TABLE 1

| $DC_{50}$ values for TO displacement from G4-RNA EBNA1 by various ligands. | |
|---|---|
| Compound | $DC_{50}$ (μM) |
| 2a | 0.26 ± 0.05 |
| 2c | 0.39 ± 0.02 |
| 3b | 0.74 ± 0.03 |
| 3c | 0.72 ± 0.03 |
| 8a | 0.61 ± 0.11 |
| 8c | 0.71 ± 0.10 |
| 9b | 0.80 ± 0.01 |
| 9c | 1.09 ± 0.10 |
| 10a | 0.32 ± 0.02 |
| 11a | 0.30 ± 0.03 |
| 11c | 0.34 ± 0.02 |
| 12b | 0.59 ± 0.03 |
| 12c | 0.65 ± 0.06 |

These data indicate that compounds 2a, 2c, 10a, 11a and 11c have a particularly high affinity for the G-quadruplex structure of EBNA1.

III. FRET (Förster Resonance Energy Transfer)-Melting Assay

1. Principle

Figure 2:
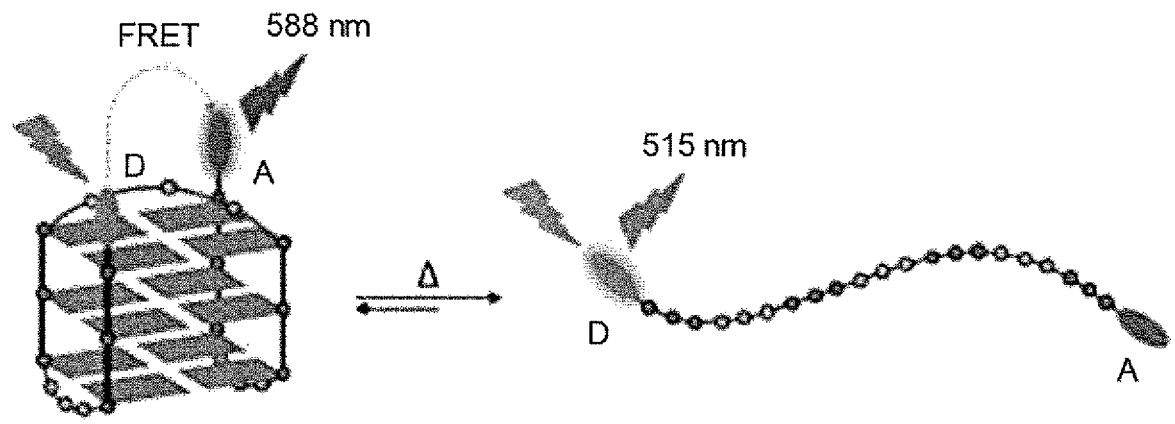
FIG. 2 shows a scheme representing the principles of a FRET-melting assay, where ☐D☐ stands for a donor fluorophore (FAM) and EALstands for an acceptor fluorophore (TAMRA).
Figure 3:
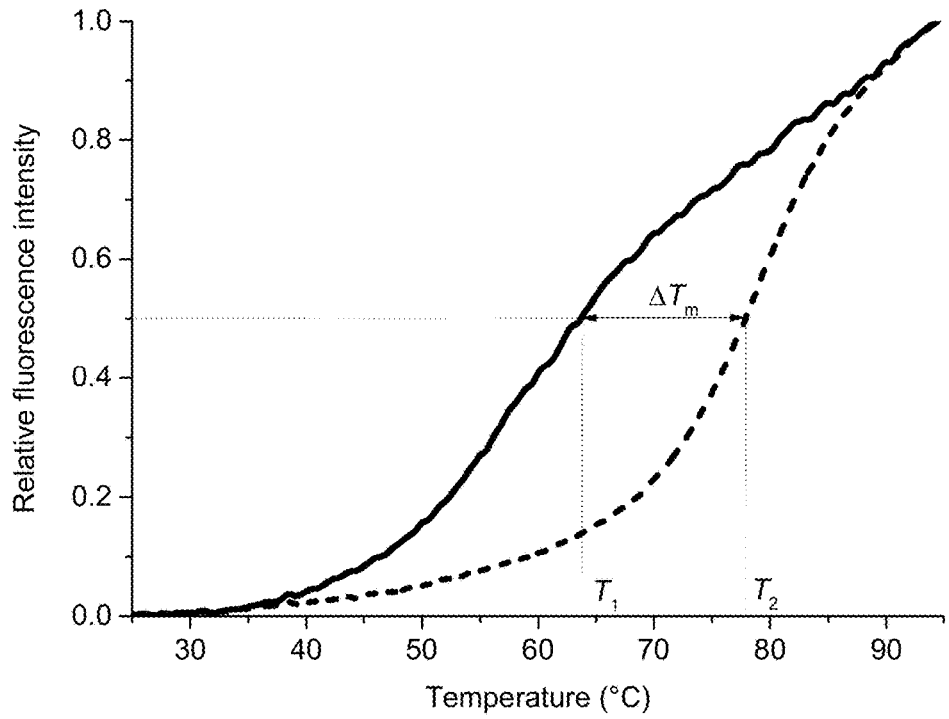
FIG. 3 shows an example of a melting curve quadruplex RNA F-EBNA1-T (0.2 µM, in $K^+$10 buffer) alone (solid line) and in the presence of compound 2a (1.0 µM) (dashed line).

The FRET-melting assay is based on thermal denaturation of G4-ARN monitored by fluorescence due to the phenomenon of Förster Resonance Energy Transfer (FRET). This method uses quadruplex-forming RNA sequence dual-labeled with two different fluorophores: a donor (fluorescein, or FAM) and an acceptor (tetramethylrhodamine, or TAMRA). When RNA is folded into G-quadruplex (G4) structure, fluorescence of the donor fluorophore is weak due to strong energy transfer (FRET) to the neighboring acceptor fluorophore. Upon thermal denaturation, the quadruplex unfolds and the fluorophores are separated, leading to decrease of the FRET effect and increase of the fluorescence of the donor (see FIG. 2). By following the fluorescence of the donor as a function of temperature, a melting curve of the G-quadruplex RNA can be obtained, which allows determining the temperature of denaturation at which 50% of the quadruples is unfolded ($T_1$, FIG. 3).

The FRET-melting assay allows assessing the affinity of small molecules (ligands) for the G4-RNA. The addition of a G4-ligand stabilizes the G-quadruplex structure and increases the denaturation temperature. The temperature of denaturation in the presence of ligands ($T_2$) can be compared with that obtained in the absence of ligands ($T_1$). The value of $\Delta T_m$ ($\Delta T_m = T_2 - T_1$) represents a measure of the affinity of the compounds of the invention (ligand). Generally, values of $\Delta T_m > 20°$ C. correspond to ligands of high affinity.

2. Materials and Reagents

The dual-labeled oligoribonucleotide EBNA1 [5'-FAM-r(GGGGCAGGAGCAGGAGGA)-TAMRA-3'] (SEQ ID no 2) purified by reversed-phase HPLC was purchased from Eurogentec. The donor fluorophore was 6-carboxyfluorescein (FAM) and the acceptor fluorophore was 6-carboxytetramethylrhodamine (TAMRA).

Stock solutions of the ligands (2 mM in DMSO) were used for FRET-melting assay, unless otherwise stated, and were stored at −20° C. FRET-melting measurements are performed on 7900HT Fast Real-Time PCR System (Applied Biosystems) with Microamp Fast optical 96-well reaction plate (Applied Biosystems).

3. Spectroscopic Measurements

Preparation of Oligonucleotides For FRET-melting assay, oligoribonucleotide F-EBNA1-T was dissolved in $K^+10$ buffer (10 mM lithium cacodylate buffer, pH 7.3, supplemented with 10 mM KCl and 90 mM LiCl).

Prior to use, all oligonucleotides were pre-treated by heating at 95° C. for 5 min, then rapidly cooled to 4° C. to favor the intramolecular folding by kinetic trapping. Duplex-DNA ds26 (5'CAA-TCG-GAT-CGA-ATT-CGA-TCC-GAT-TG-3') (SEQ ID no 3) was prepared by heating this self-complementary strand at 90° C. for 5 min in $K^+10$ buffer followed by a slow cooling over 6 h.

FRET-Melting Experiments

FRET-melting assay is performed in 96-well plates on real time PCR apparatus 7900HT Fast Real-Time PCR System using the heating ramp as follow: 5 min at 25° C., then increase of 0.5° C. every minute until 95° C. Each experimental condition was tested in duplicated in a volume of 25 μL for each sample. The 96-well plates (Applied Biosystems) were prepared by aliquoting the annealed RNA (24 μL of 0.21 μM solution in $K^+10$ buffer) into each well, followed by 1 μL of ligand solution (25 μM in $K^+10$ buffer). For competition experiments, duplex competitors were added to 200 nM quadruplex sequences at final concentrations of 3.0 μM (15 eq) and 10.0 μM (50 eq), with a total reaction volume of 25 μL, with the labeled oligoribonucleotide (0.2 μM) and the ligand (1.0 μM). Measurements were made with excitation at 492 nm and detection at 516 nm. The change in the melting temperature in the presence of 1.0 μM putative ligand, $\Delta T_m$ (1.0 μM), was calculated from at least two experiments by subtraction of the blank from the averaged melting temperature of each compound (1.0 μM).

4. Results

Figure 4:
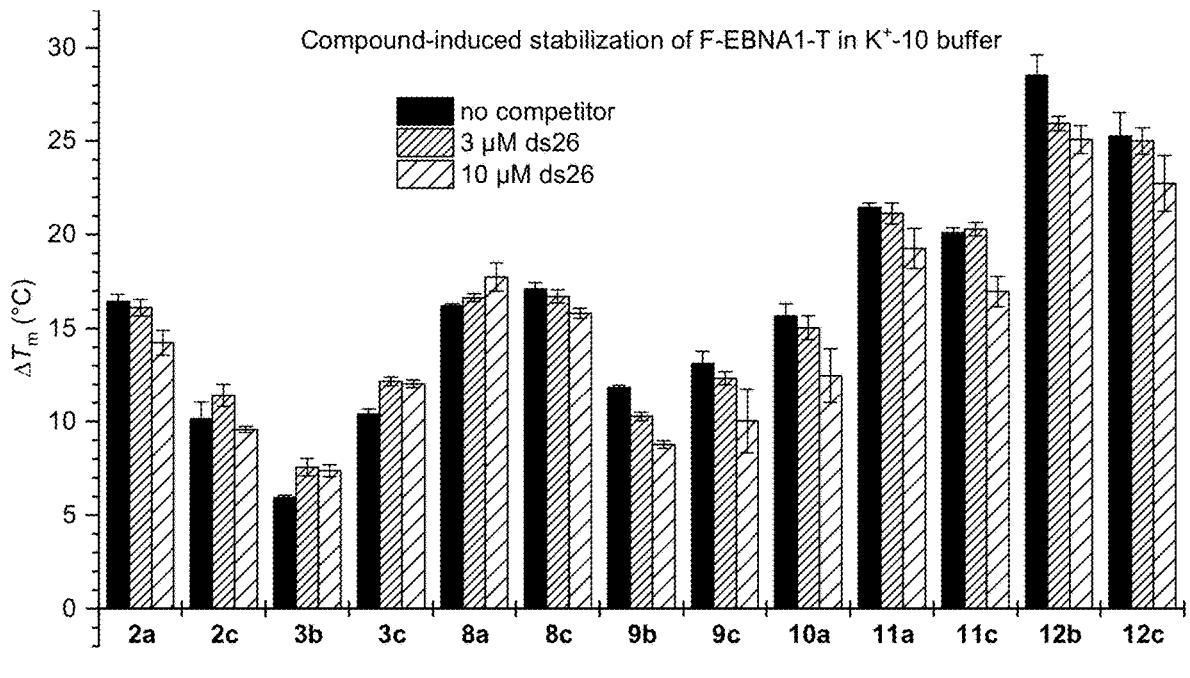
FIG. 4 shows a bar graph of the stabilization of F-EBNA1-T (0.2 µM), expressed as $\Delta T_m$ (° C.) values, by compounds of the invention (1.0 µM) in $K^+$10 buffer in the presence of increasing concentrations of competitor DNA ds26 (SEQ ID no 3) (0, 15 and 50 molar equivalents).

The results are shown in FIG. 4 and in Table 2 below (higher $\Delta T_m$ values indicate higher affinity of the compounds to G4-RNA structure of EBNA1). These results are based on triplicate assays.

TABLE 2

| Compound | $\Delta T_m$ (° C.) Ligand alone | Ligand + 3 μM ds26 | Ligand + 10 μM ds26 |
| --- | --- | --- | --- |
| 2a | 16.4 ± 0.4 | 16.1 ± 0.4 | 14.2 ± 0.7 |
| 2c | 10.1 ± 0.9 | 11.4 ± 0.6 | 9.6 ± 0.2 |
| 3b | 5.9 ± 0.1 | 7.6 ± 0.5 | 7.4 ± 0.3 |

TABLE 2-continued

| Compound | $\Delta T_m$ (° C.) Ligand alone | Ligand + 3 μM ds26 | Ligand + 10 μM ds26 |
| --- | --- | --- | --- |
| 3c | 10.4 ± 0.3 | 12.2 ± 0.2 | 12.0 ± 0.2 |
| 8a | 16.2 ± 0.1 | 16.6 ± 0.2 | 17.7 ± 0.8 |
| 8c | 17.1 ± 0.3 | 16.7 ± 0.3 | 15.8 ± 0.3 |
| 9b | 11.8 ± 0.1 | 10.3 ± 0.2 | 8.8 ± 0.2 |
| 9c | 13.1 ± 0.6 | 12.3 ± 0.4 | 10.0 ± 1.7 |
| 10a | 15.7 ± 0.6 | 15.0 ± 0.6 | 12.5 ± 1.5 |
| 11a | 21.5 ± 0.2 | 21.1 ± 0.6 | 19.3 ± 1.1 |
| 11c | 20.1 ± 0.3 | 20.3 ± 0.4 | 17.0 ± 0.8 |
| 12b | 28.5 ± 1.1 | 25.9 ± 0.4 | 25.1 ± 0.8 |
| 12c | 25.3 ± 1.3 | 25.0 ± 0.7 | 22.7 ± 1.5 |

These data indicate that compounds 2a, 8a, 8c, 10a, 11a, 11c, 12b and 12c have a particularly high affinity for the G-quadruplex structure of EBNA1.

IV. Yeast Assay

Compounds 1a, 2a, 4a, 5a, 7a, 10a and 11a were also tested in the various assay described in Lista et al. (*Nat Commun* 2017, 8, 16043). All compounds gave positive results in this assay.

The results obtained with compounds 2a and 11a are detailed below.

SDS-PAGE and Western Blot Analysis

The aim of these experiments is to assess the effect of the inventive compounds on the GAr-based inhibition of protein expression. For this purpose, H1299 cells were transfected by plasmids allowing expression of either EBNA1 or, as a control EBNA1ΔGAr and then treated, or not by various concentrations of the indicated compounds. As GAr inhibits the translation of its own mRNA, EBNA is significantly less expressed than EBNA1ΔGAr leading to a weaker steady state level of the EBNA1 protein as compared to EBNA1ΔGAr. Compounds able to interfere with GAr-based inhibition of translation will increase the steady state level of EBNA1, whereas a having no effect on EBNA1ΔGAr.

Figure 5:
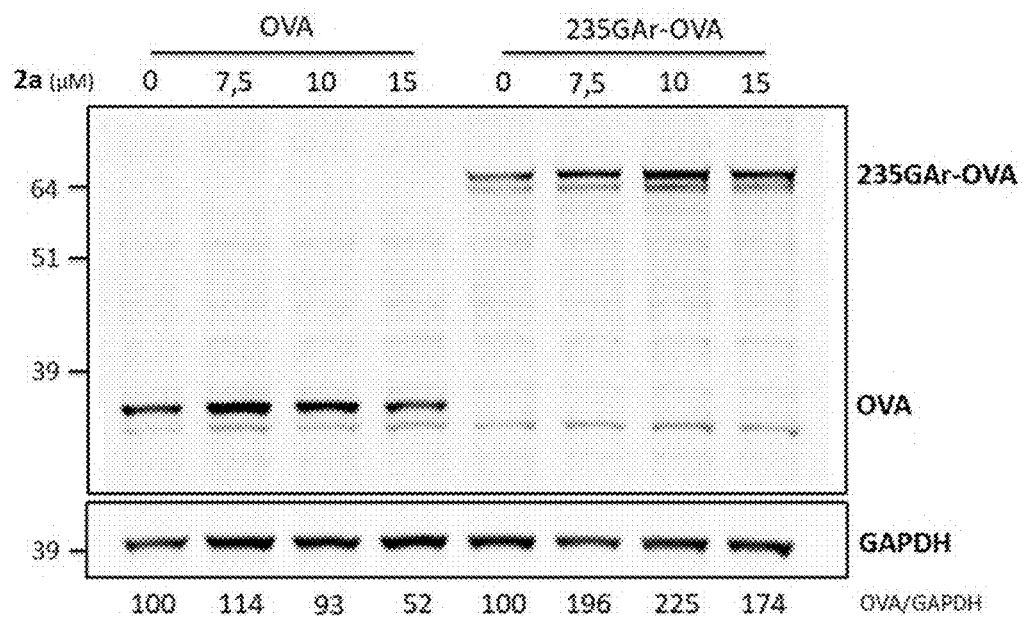

Results are shown in FIG. 5. Treatment with compound 2a led to a significant increase in the steady-state level of 235GAr-OVA in H1299 cells in a dose-dependent manner. This effect is GAr-dependent since compound 2a had no significant effect on OVA expression. The ratio of the quantity of OVA or GAr-OVA relatively to GAPDH (the loading control) are indicated below the gel.

Therefore, compound 2a interferes with the GAr-based inhibition of protein expression. Interference with EBNA1 expression in EBV-infected cells was assessed in different cell lines. The principle of these experiments is the same than the one described in the paragraph just above except that the steady state level of endogenous EBNA1 is determined in these EBV-infected cell lines. Hence these tests are closer to the reality but, of course, there is no possibility of EBNA1ΔGAr controls in these experiments.

B95.8 cells are derived from cotton-top Tamarin Monkey peripheral blood lymphocyte EBV-positif. Mutu-1 cells are derived from an EBV-positive Burkitt's lymphoma biopsy specimen from a Kenyan patient. Raji cells are EBV-positive type III latency Burkitt's lymphoma.

Figure 6:
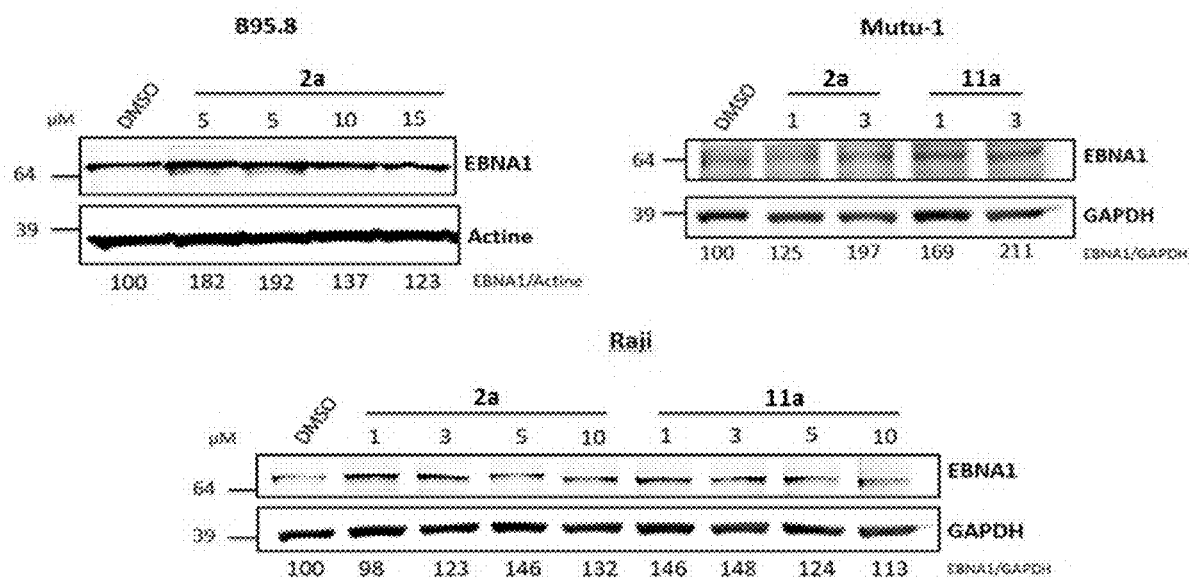
FIG. 6 shows western blots identifying the presence of protein EBNA41 relatively to GAPDH or Actine in different cell lines (namely B95.8, Mutu-1 and Raji), after treatment with compound 2a (B95.8, Mutu-1 and Raji) or compound 11a (Raji).
Figure 7:
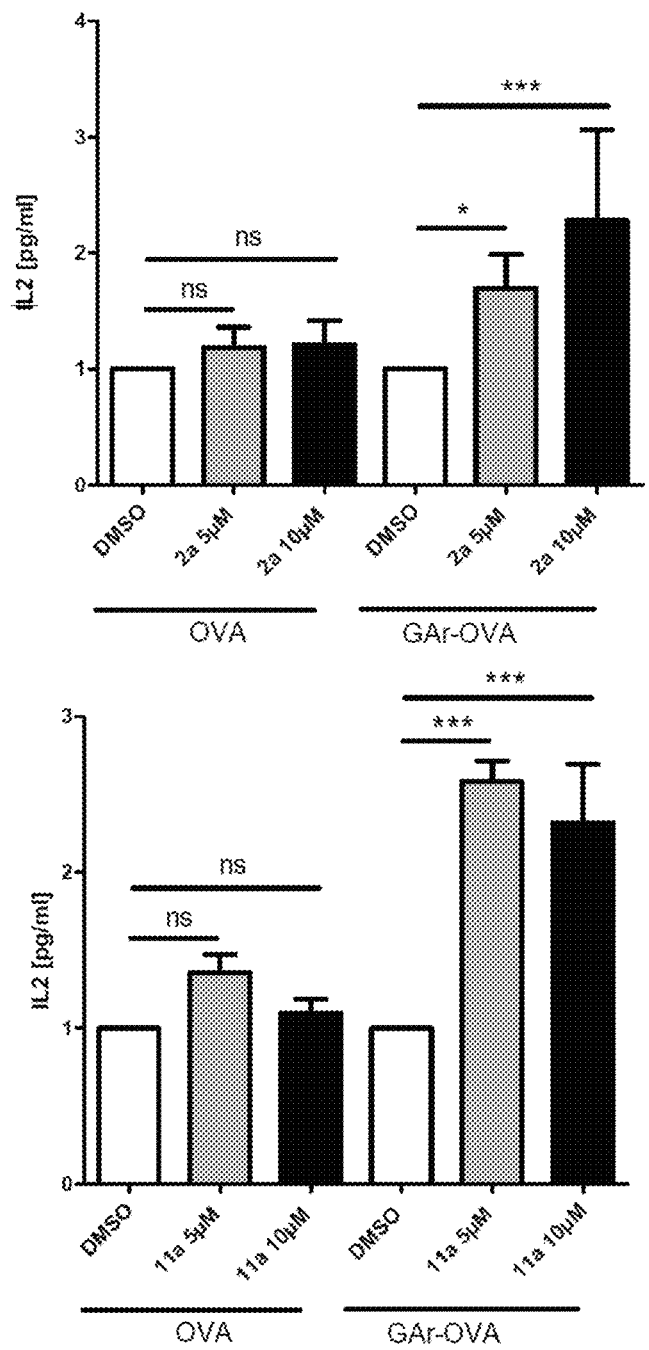
FIG. 7 shows the IL2 concentration (in pg/mL) respectively with DMSO (control), 5 µM and 10 µM of compound 2a in DMSO with OVA and Gar-OVA (left), or with DMSO (control), 5 µM and 10 µM of compound 11a in DMSO with OVA and Gar-OVA (right). Stars indicate significant results (the higher the number of stars, the more significant). "ns" stands for not significant.
Figure 8:
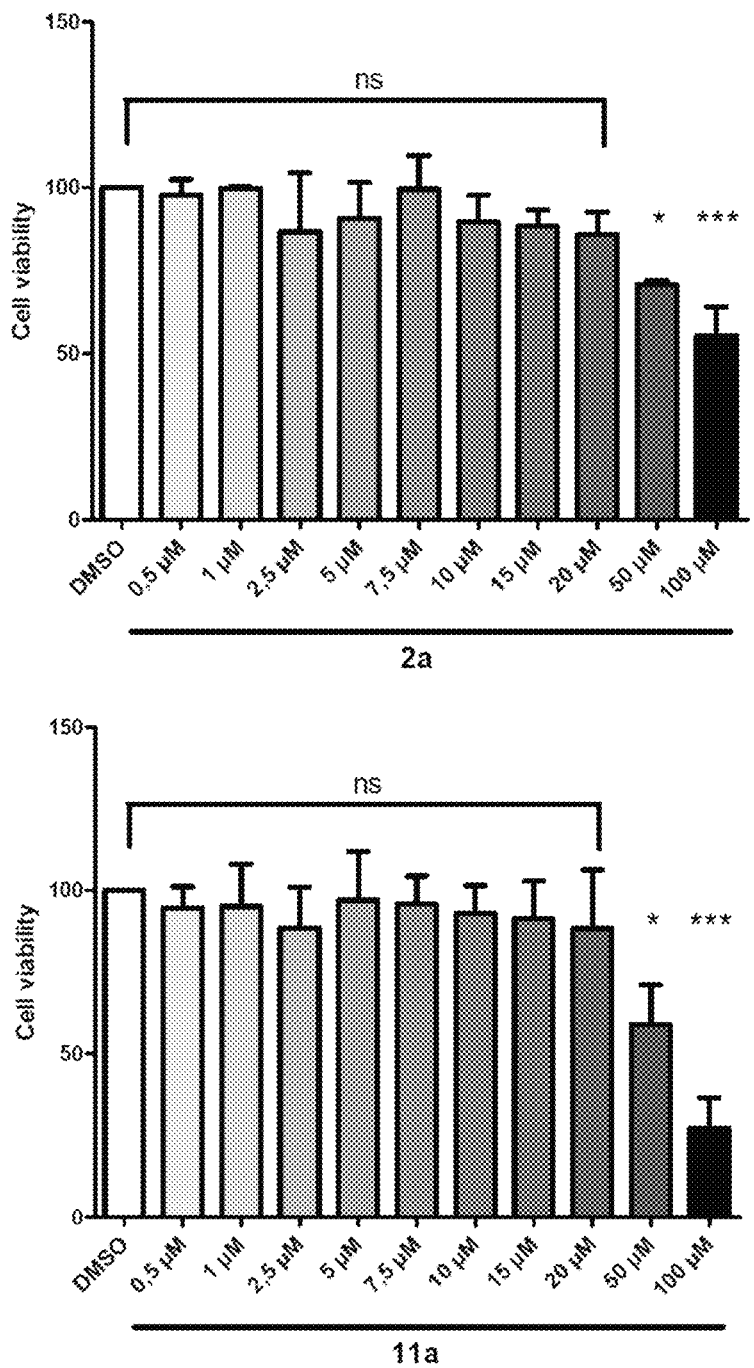
FIG. 8 shows the cell viability (in %) for the control (DMSO) and various concentrations of compound 2a (left), or for the control (DMSO) and various concentrations of compound 11a (right). Stars indicate significant results (the higher the number of stars, the more significant).
Figure 9:
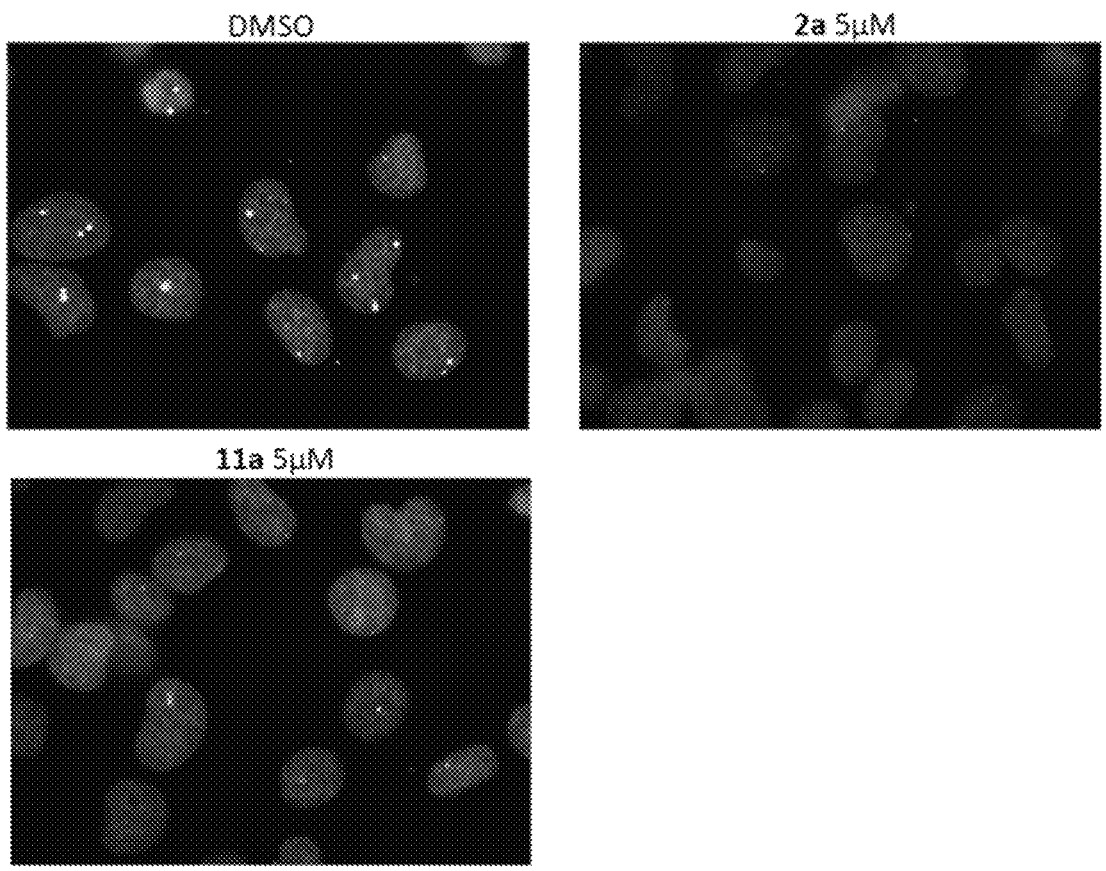
FIG. 9 shows the proximity ligation assay (PLA) performed in H1299 cells transfected with EBNA1 plasmids and treated respectively with pure DMSO (control assay), 5 µM of compound 2a in DMSO, and with 5 µM of compound 11a in DMSO.
Figure 10:
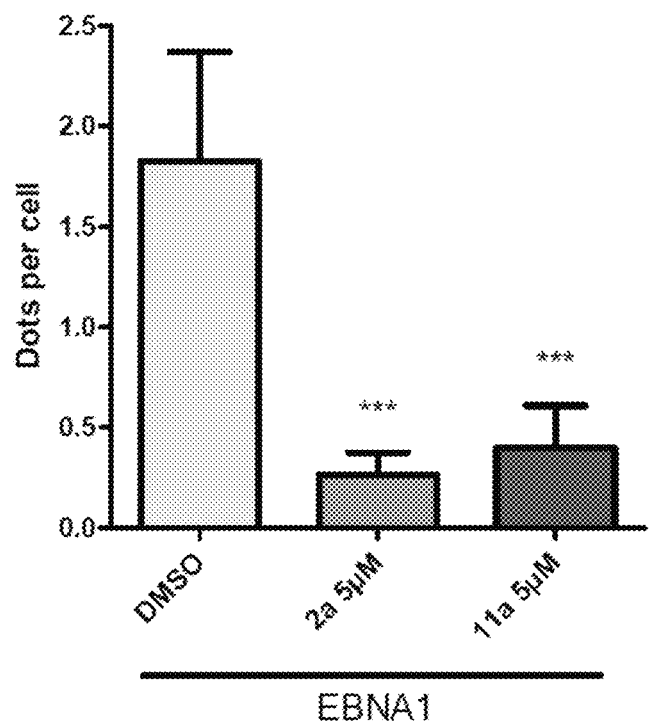
FIG. 10 shows the number of nuclear PLA dots per cell (transfected with EBNA1 plasmids) treated respectively with pure DMSO (control assay), 5 µM of compound 2a in DMSO, and with 5 µM of compound 11a in DMSO. Stars indicate significant results (the higher the number of stars, the more significant).

Results are shown in FIG. 6. Compounds 2a and 11a increase in a GAr-dependent manner EBNA1 expression in EBV-infected cells.

Antigen Presentation Assay

The aim of this assay was to determine if compounds 2a and 11a were able to interfere (suppress) with the GAr-dependent limitation of EBNA1-derived antigenic peptid presentation. H1299 cells were transfected with 235GAr-OVA or OVA plasmids and murine MHC class I Kb plasmids. T-cell proliferation is determined using ELISA assay for Mouse IL-2 (IL-2 is a potent lymphoid cell growth factor which exerts its biological activity primarily in T cell). There is therefore a correlation between the quantity of IL2 released and the T-cell proliferation.

Quantifications of IL2 release following treatment with compounds 2a or 11a, as compared to DMSO-treated cells are shown in the FIG. 7. Compounds 2a and 11a significantly increased (two-fold change) the release of IL-2 added for H1299 cells expressing 235GAr-OVA, whereas it had no effect on IL-2 release with OVA-expressing cells. These compounds thus increase T-cell proliferation. In other words, compounds 2a and 11a significantly activates GAr-limited antigen presentation.

Cell Viability (MTT Assay)

Toxicity of various concentration of G4 ligands on Mutu-1 cells was assessed using the classical MTT assay. The results obtained with various concentrations of compounds 2a and 11a were compared to the result obtained with cells treated by DMSO (compound vehicle).

Results are shown in FIG. 8. Preliminary results indicate that compounds 2a and 11a are not significantly toxic on Mutu-1 cells when used at a concentration range (3110 μM) where they increase the expression of EBNA1.

Proximity Ligation Assay (PLA)

The aim of PLA is to assess if compounds 2a and 11a (like PhenDC3) do interfere with the ability of nucleolin (NCL) to interact with the G4s of the EBNA1 mRNA, hence leading to the GAr-dependent limitation of EBNA1 expression. We previously showed that NCL and EBNA1 mRNA do interfere using PLA (ref.: Proximity ligation assays: a recent addition to the proteomics toolbox. Weibrecht I Expert Rev Proteomics. 2010 doi: 10.1586/EPR.10.10) and that NCL directly interacts with the G-quadruplexes formed in the GAr-encoding sequence of EBNA1 mRNA (Lista et al. (*Nat Commun* 2017, 8, 16043). Using PLA, we also showed in this study that this interaction is prevented by PhenDC3. We show here, as shown in FIG. 9, that both compounds 2a and 11a significantly reduce both the number of PLA dots and their intensity, hence confirming the ability of these new GA ligands to interfere with GAr-dependent limitation of EBNA1 expression and antigenic presentation. These results also strongly suggest that compounds 2a and 11a, similarly to PhenDC3, act by preventing NCL to interact with EBNA1 mRNA's G4s.

As shown in FIG. 10, the number of nuclear PLA dots per cell was significantly reduced when H1299 cells transfected with EBNA1 plasmids were treated with 5 μM of compounds 2a or 11a.

Compounds 2a and 11a prevent the interaction between NCL- and the G4s of EBNA1 mRNA.

Conclusions

Compounds 2a and 11a both increase EBNA1 expression and GAr-dependent antigen presentation, probably by the same mechanism of action as PhenDC3 (Lista et al., *Nat Commun* 2017, 8, 16043), namely by binding to the G4 form of EBNA1 mRNA and preventing the binding of NCL thereon.

V. Conclusion

The tested compounds 2a and 11a were shown to be effective in interacting in vitro with RNA G4 quadruplexes of EBNA1 protein. They were also shown to be effective in disrupting the ability of NCL to interact with the G-quadruplexes formed in the GAr-encoding sequence of EBNA1 mRNA, an interaction at the basis of the the GAr-based mechanism allowing EBNA1 immune evasion.

Hence, altogether these results demonstrate their potency for unveiling EBV-infected tumour cells to the host immune system, in particular by preventing the limitation of EBNA1 production in EBV-infected cells. Thus, they show their potency as therapeutic agents for preventing and/or treating EBV-related cancer.

The invention claimed is:

1. A compound of formula (I), or a hydrate or a solvate thereof:

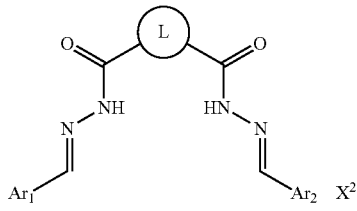

(I)

wherein

Ar₁ and Ar₂ may be identical or different and are each independently selected from the group consisting of groups of formula (II) and (III):

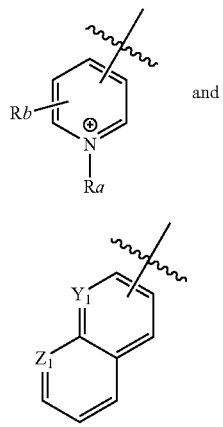

(II)

and (III)

$R_a$ is $C_1$-$C_6$ alkyl, optionally substituted with a OH group, a O—($C_1$-$C_4$)alkyl group or a monocyclic or bicyclic 5- to 10-membered aromatic or heteroaromatic group, $R_b$ is a hydrogen atom, a halogen atom, $C_1$-$C_6$ alkyl optionally substituted with a OH group, or a O—($C_1$-$C_4$)alkyl group, $Y_1$ and $Z_1$ are independently CH or $N^+$—$R_c$, provided that at least one of $Y_1$ and $Z_1$ is $N^+$—$R_c^+$ and at least one of $Y_1$ and $Z_1$ is CH, $R_c$ is $C_1$-$C_6$ alkyl, optionally substituted with a OH group, a O—($C_1$-$C_4$)alkyl group, or a monocyclic or bicyclic 5- to 10-membered aromatic or heteroaromatic group, $X^{2-}$ is one or a plurality of pharmaceutically acceptable anion(s), selected so as to obtain an overall electrically neutral salt, L is (A), (C) or (E):

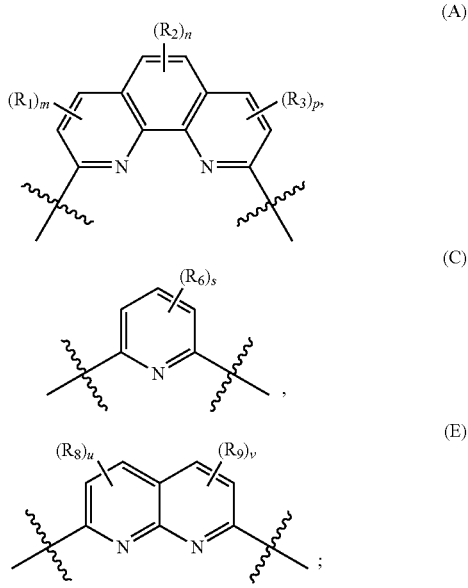

provided that Ar₁ and Ar₂ are not groups of formula (II) when L is (C) or (E), m, n, p, u and v may be identical or different and are each independently an integer selected from 0 to 2;

s is an integer selected from 0 to 3;

$R_1$, $R_2$, $R_3$, $R_6$, $R_8$ and $R_9$ may be identical or different and are each independently a halogen atom, a $C_1$-$C_6$ alkyl group, a $C_3$-$C_8$ cycloalkyl group, a O($C_1$-$C_6$)alkyl group, a $NR_{10}R_{11}$ group, a $C_2$-$C_6$ alkenyl group, or a $C_5$-$C_8$ cycloalkenyl group, said $C_1$-$C_6$ alkyl group, $C_3$-$C_8$ cycloalkyl group, O($C_1$-$C_6$)alkyl group, $C_2$-$C_6$ alkenyl group, or $C_5$-$C_8$ cycloalkenyl group being optionally substituted with one to three halogen atoms, a OH group, a O—($C_1$-$C_6$)alkyl group, a NH—($C_1$-$C_6$)alkyl group or a NHC(O)—R';

$R_{10}$ and $R_{11}$ may be identical or different and are each independently:

a hydrogen atom, a $C_1$-$C_6$ alkyl group optionally substituted with a OH group, a O—($C_1$-$C_6$)alkyl group, a NH—($C_1$-$C_6$) alkyl group or a NHC(O)—R', or $NR_{10}R_{11}$, taken together, form a 3- to 8-membered heterocycloalkyl or 5- to 8-membered heterocycloalkenyl, R' is a ($C_1$-$C_6$)alkyl group optionally substituted with a $C_5$-$C_{10}$ aryl group, wherein said $C_5$-$C_{10}$ aryl group is optionally substituted with a halogen atom, a $C_1$-$C_6$ alkyl group, a O($C_1$-$C_6$)alkyl group, a $C_2$-$C_6$ alkenyl group, a $C_5$-$C_8$ cycloalkenyl group, a 3- to 8-membered heterocycloalkyl, a 5- to 8-membered heterocycloalkenyl, a $N((C_1-C_6)alkyl)_2$ group or a $N((C_1-C_6)haloalkyl)_2$ group.

2. The compound of claim 1, wherein $Ar_1$ and $Ar_2$ may be identical or different and are each independently selected from the group consisting of groups of formula (II'), (III') and (III''):

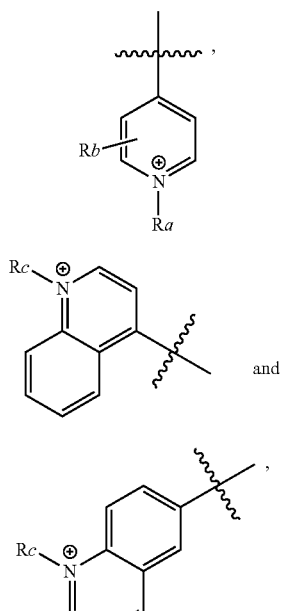

With $R_a$, $R_b$ and $R_c$ as defined in claim 1.

3. The compound of claim 1 or a hydrate or a solvate thereof, wherein $Ar_1$ and $Ar_2$ are identical.

4. The compound of claim 1, or a hydrate or a solvate thereof, wherein $Ar_1$ and/or $Ar_2$ is of formula (II), $R_a$ is a linear $C_1-C_4$ alkyl optionally substituted with a phenyl group, and $R_b$ is a hydrogen or halogen atom;
or wherein $Ar_1$ and/or $Ar_2$ are of formula (III), and $R_c$ is a linear $C_1-C_4$ alkyl optionally substituted with a phenyl group.

5. The compound of claim 1, or a hydrate or a solvate thereof, wherein $X^{2-}$ represents two anions selected from the group consisting of a halogenide, a carboxylate, a $C_1-C_6$alkylsulfonate, a $C_1-C_6$haloalkylsulfonate and an alkylarylsulfonate.

6. The compound of claim 1, or a hydrate or a solvate thereof, wherein L is (C), s is 0, and $Ar_1$ and $Ar_2$ are identical and of formula (III).

7. The compound of claim 1, or a hydrate or a solvate thereof, wherein L is (A), $Ar_1$ and $Ar_2$ are identical and of formula (II) or (III), and
   m and p are 0, and n is 0 or 1, or
   m and n are 0, and p is 0 or 1, or
   n is 0, and m and p are identical and are 0 or 1, or
   m, n and p are 0.

8. The compound of claim 1, or a hydrate or a solvate thereof, wherein L is (E) and u and v are 0.

9. The compound of claim 1, or a hydrate or a solvate thereof, wherein it is:

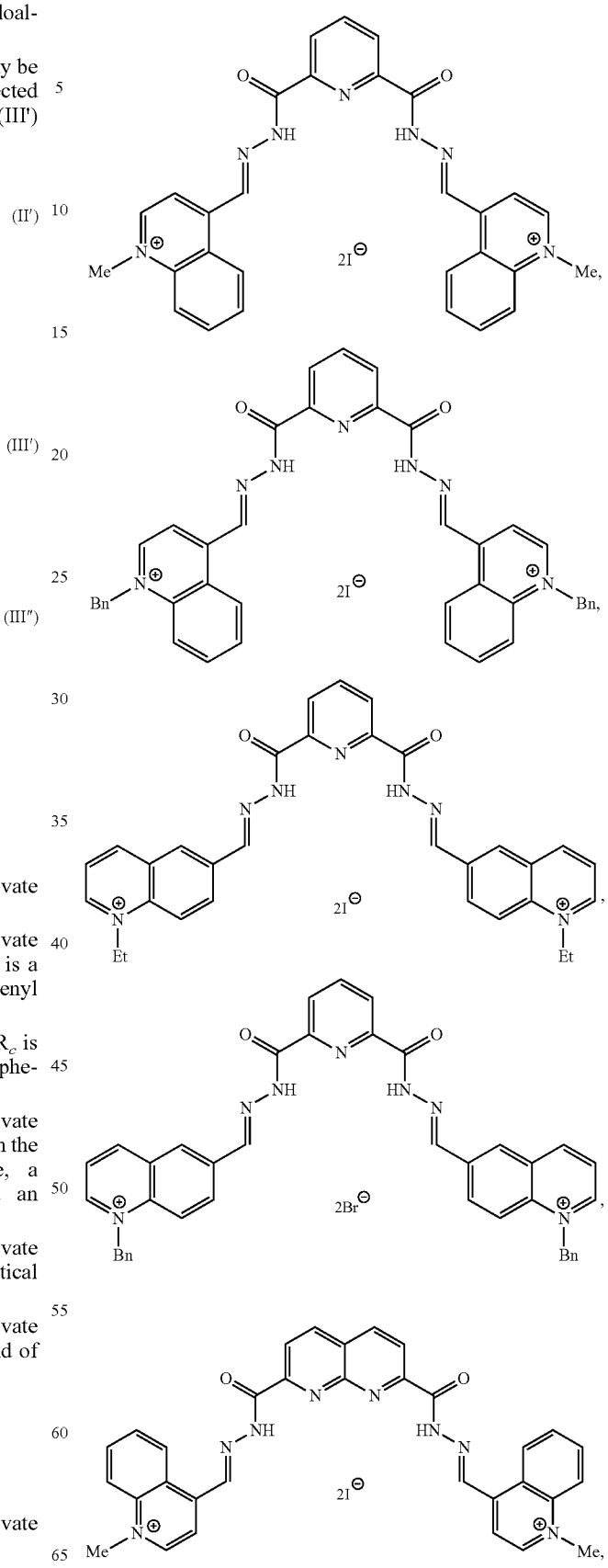

-continued

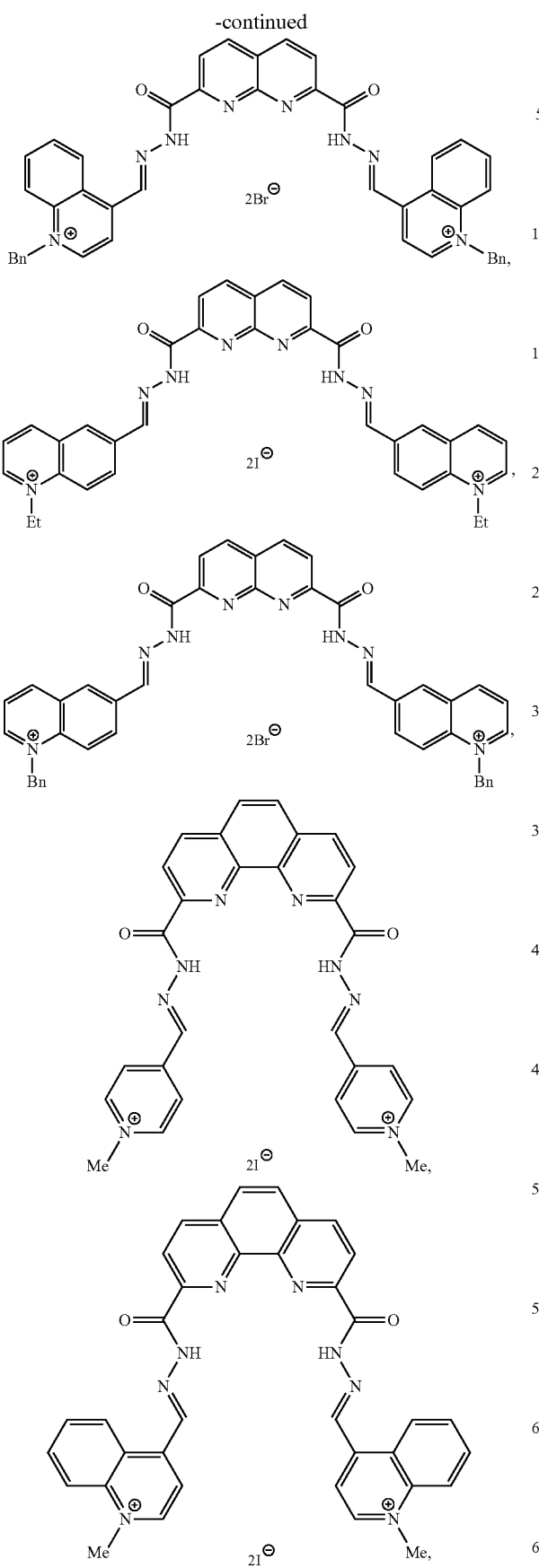

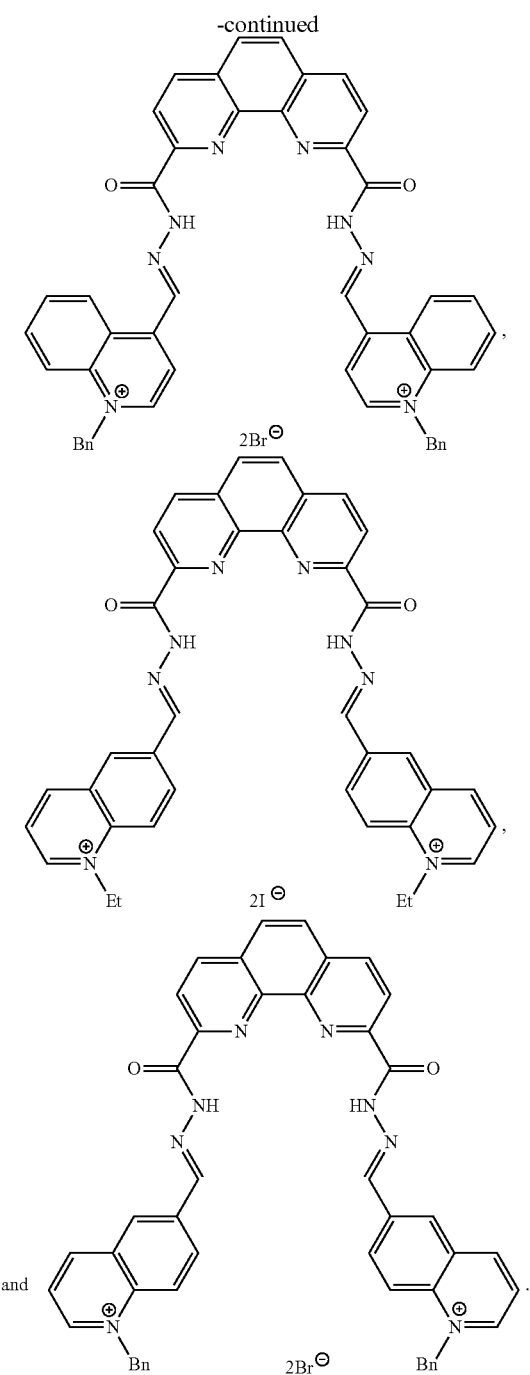

10. A composition comprising:
   as active ingredient, the compound of formula (I) as defined in claim 1, or a hydrate or a solvate thereof, and optionally another therapeutic agent selected from antibiotics, anticancer agents, and steroidal and non-steroidal anti-inflammatory drugs, and
   a pharmaceutically acceptable excipient.

11. The composition of claim 10, wherein the pharmaceutically acceptable excipient is suitable for injection.

12. A method for treating an Epstein-Barr-Virus (EBV)-related cancer, comprising the administration of an effective amount of the compound of claim 1.

13. A method for treating an Epstein-Barr-Virus (EBV)-related cancer, comprising the simultaneous, staggered or sequential administration as a combination product of a kit comprising at least:
   a first composition comprising the compound of formula (I) as defined in claim 1, or a hydrate or a solvate thereof, and a pharmaceutically acceptable excipient, and
   a second composition comprising another therapeutic agent.

14. The method of claim 12, wherein the EBV-related cancer is a Hodgkin's lymphoma, a Burkitt's lymphoma, a nasopharyngeal carcinoma, a gastric cancer, lymphomas in immunosuppressed patients, or T/NK cell lymphomas.

15. The compound of claim 4, or a hydrate or a solvate thereof, wherein $R_a$ is an ethyl, a methyl group or a benzyl group.

16. The compound of claim 4, or a hydrate or a solvate thereof, wherein $R_c$ is an ethyl, a methyl group or a benzyl group.

17. The compound of claim 6, or a hydrate or a solvate thereof, wherein $Ar_1$ and $Ar_2$ are identical and of formula

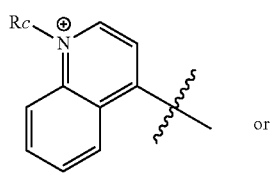
(III')

or

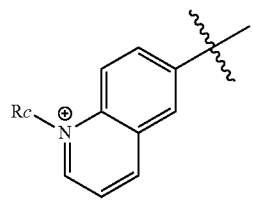
(III'')

18. The compound of claim 7, or a hydrate or a solvate thereof, wherein $Ar_1$ and $Ar_2$ are identical and of formula

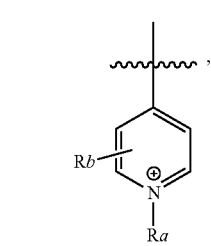
(II')

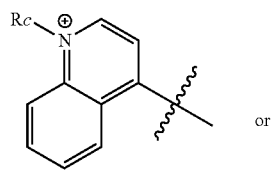
(III')

or

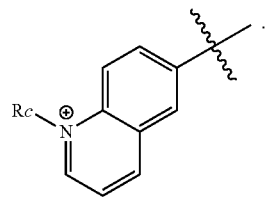
(III'')

19. The compound of claim 1, or a hydrate or a solvate thereof, wherein it is:

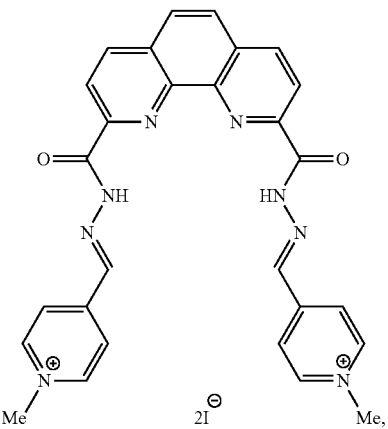

-continued

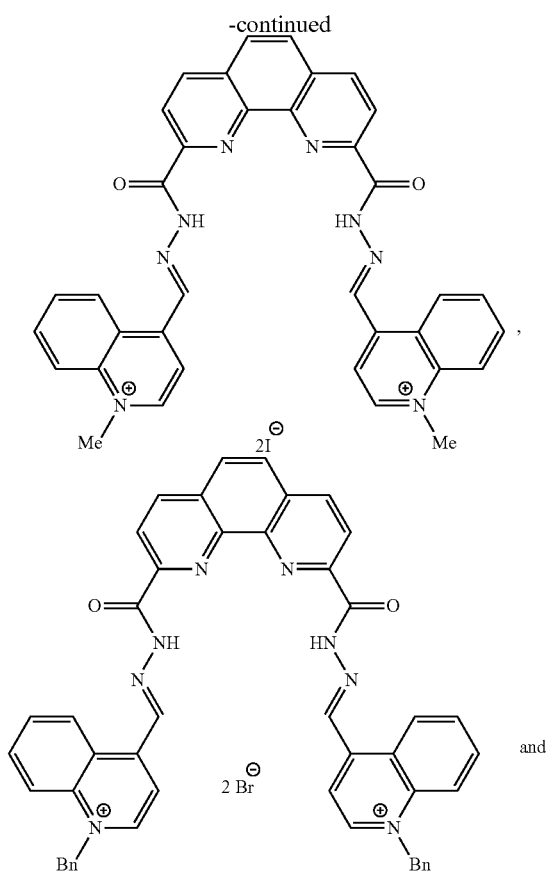

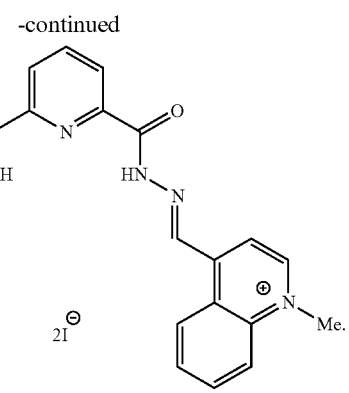

20. A method for treating an Epstein-Barr-Virus (EBV)-related cancer, comprising the administration of an effective amount of the composition of claim 10.

21. The method of claim 13, wherein the other therapeutic agent is selected from antibiotics, anticancer agents, and steroidal and non-steroidal anti-inflammatory drugs.

22. The method of claim 13, wherein the EBV-related cancer is a Hodgkin's lymphoma, a Burkitt's lymphoma, a nasopharyngeal carcinoma, a gastric cancer, lymphomas in immunosuppressed patients, or T/NK cell lymphomas.

23. The method of claim 20, wherein the EBV-related cancer is a Hodgkin's lymphoma, a Burkitt's lymphoma, a nasopharyngeal carcinoma, a gastric cancer, lymphomas in immunosuppressed patients, or T/NK cell lymphomas.

* * * * *